United States Patent [19]

Fischer et al.

[11] Patent Number: 5,504,213

[45] Date of Patent: Apr. 2, 1996

[54] BENZOFURANYL-AND-THIOPHENYL-ALKANECARBOXYCLIC ACID DERIVATIVES

[75] Inventors: Rüdiger Fischer; Gabriele Bräunlich; Klaus-Helmut Mohrs, all of Wuppertal; Rudolf Hanko, Essen; John-Edward Butler-Ransohoff; Mazen Es-Sayed, both of Wuppertal, all of Germany; Graham Sturton, Bray Maidenhead, Great Britain; Steve Tudhope, Windsor, Great Britain; Trevor Abram, Marlow, Great Britain; Wendy J. McDonald-Gibson, Ewelme Wallingford, Great Britain

[73] Assignee: Bayer Aktiengesellschaft, Leverkusen, Germany

[21] Appl. No.: 236,796

[22] Filed: Apr. 29, 1994

[30] Foreign Application Priority Data

May 6, 1993 [GB] United Kingdom ............. 9309324

[51] Int. Cl.[6] ............... C07D 407/06; C07D 307/83; C07D 333/72; A61K 31/35; A61K 31/40; A61K 31/445

[52] U.S. Cl. ............. 548/253; 514/382; 514/326; 514/469; 514/422; 546/214; 548/525; 549/467; 549/218; 549/468

[58] Field of Search ............. 548/525; 549/467, 549/468, 218, 55; 546/214; 514/326, 382, 422, 469

[56] References Cited

U.S. PATENT DOCUMENTS 4,663,347  5/1987  Atkinson et al. ............. 514/467

FOREIGN PATENT DOCUMENTS 0019955  10/1980  European Pat. Off. .
0145234  4/1985  European Pat. Off. .

OTHER PUBLICATIONS

Bulletin of the Chemical Society of Japan, vol. 49(3), 737–740, Mar. 1976 Takaaki Horaguchi.

*Primary Examiner*—David B. Springer
*Attorney, Agent, or Firm*—Sprung Horn Kramer & Woods

[57] ABSTRACT

The Benzofuranyl- and -thiophenyl-alkane-carboxylic acid derivatives are prepared Tby cyclisation of hydroxy acetophenones and related compounds or by Wittig-reaction of benzofuranyl aldehydes. The compounds can be used to prepared medicaments.

11 Claims, No Drawings

BENZOFURANYL-AND-THIOPHENYL-ALKANECARBOXYCLIC ACID DERIVATIVES

The invention relates to benzofuranyl- and -thiophenyl-alkanecarboxyclic acids derivatives, processes for their preparation and their use in medicaments.

It is known that the NADPH oxidase of phagocytes is the physiological source to the superoxide radical anion and reactive oxygen species derived therefrom which are important in the defence against pathogens. Uncontrolled formation leads to tissue damage in inflammatory processes. It is additionally known that elevation of phagocyte cyclic AMP leads to inhibition of oxygen radical production and that this cell function is more sensitive than others such as aggregation or enzyme release (cf. Inb. Arch. Allergy Immunol., vol. 97: pp 194–199, 1992).

Benzofuran- and benzothiophene derivatives having lipoxygenase-inhibiting action are described in the publication EP 146 243.

Surprisingly it was found that compounds given by the general formula (I) inhibited oxygen radical formation and elevated cellular cyclic AMP levels probably by inhibition of phagocyte phosphodiesterase activity.

The invention relates to benzofuranyl- and -thiophenyl-alkanecarboxyclic acids derivatives of the general formula (I)

$$\text{(I)}$$

in which
- $R^1$ and $R^2$ are identical or different and represent hydrogen, halogen, carboxyl, cyano, nitro, trifluoromethyl or a group of a formula $—OR^4$, $—SR^5$ or $—NR^6R^7$, in which
  - $R^6$ denotes hydrogen or straight-chain or branched alkyl having up to 4 carbon atoms,
- $R^4$, $R^5$ and $R^7$ are identical or different and denote hydrogen, cycloalkyl having 3 to 6 carbon atoms, or a 5 to 7-membered saturated or unsaturated heterocycle having up to 3 heteroatoms from the series comprising N, S and O, which are optionally substituted by identical or different substituents from the series comprising halogen, cyano, nitro or by straight-chain or branched alkyl or alkoxycarbonyl each having up to 6 carbon atoms, or denote a residue of formula or denote straight-chain or branched alkyl or alkenylen each having up to 8 carbon atoms, and each of which is optionally monosubstituted to trisubstituted by identical or different substituents from the series comprising trifluoromethyl, difluoromethyl, halogen, cyano, carboxy, hydroxy, straight-chain or branched alkoxy, alkoxycarbonyl or acyl each having up to 6 carbon atoms or by a 5- to 7-membered saturated or unsaturated heterocycle having up to 3 hetero atoms from the series comprising N, S and O and to which an aromatic ring can be fused, or by N-methyl-substituted imidazolyl or by a residue of formula phenyl, wherein all rings are optionally monosubstituted to trisubstituted by identical or different substituents from the series comprising nitro, halogen, carboxy or straight-chain or branched alkyl or alkoxycarbonyl each having up to 6 carbon atoms, or alkyl or alkenylen are substituted by a group of formula $—CO—NR^8R^9$ in which
  - $R^8$ and $R^9$ are identical or different and denote phenyl, adamantyl, cycloalkyl having up 3 to 7 carbon atoms, benzyl, formyl, hydrogen, straight-chain or branched alkyl or alkenyl each having up to 6 carbon atoms and which are optionally substituted by carboxy, hydroxy or straight-chain or branched alkoxycarbonyl up to 6 carbon atoms or
  - $R^8$ and $R^9$ together with the nitrogen atom form a 5 to 7 membered saturated or unsaturated heterocycle, or
- $R^4$ denotes a protecting group of a hydroxyl group, difluoromethyl or a group of a formula $—SO_2—X$ in which
  - X denotes trifluoromethyl, phenyl or straight-chain or branched alkyl having up to 6 carbon atoms,
- T represents an oxygen or sulfur atom
- V represents a straight-chain or branched alkylene or alkenylene chain each having 2 to 8 carbon atoms,
- W represents cyano, tetrazolyl or a group of a formula $—CO—R^{10}$, $—CO—NR^{11}R^{12}$, $—CONR^{13}—SO_2—R^{14}$ or $PO(OR^{15})(OR^{16})$, or a residue of the formula in which
  - $R^{10}$ denotes hydroxyl, cycloalkyloxy having up 3 to 7 carbon atoms or straight-chain or branched alkoxy having up to 8 carbon atoms,
  - $R^{11}$, $R^{12}$ and $R^{13}$ are identical or different and denote hydrogen, phenyl or straight-chain or branched alkyl or acyl each having up to 6 carbon atoms and which are optionally substituted by hydroxyl, or
  - $R^{11}$ denotes hydrogen and
  - $R^{12}$ denotes hydroxyl or
  - $R^{11}$ and $R^{12}$ together with the nitrogen atom form a 5- or 6-membered saturated heterocycle,
  - $R^{14}$ denotes straight-chain or branched alkyl having up to 6 carbon atoms, which is optionally substituted by phenyl or trifluoromethyl, or denotes phenyl, which is optionally substituted by substituents from the series comprising halogen, cyano, nitro or by straight-chain or branched alkyl having up to 6 carbon atoms, '$R^{15}$ and $R^{16}$ are identical or different and represent hydrogen or straight-chain or branched alkyl having up to 6 carbon atoms, R³ represents phenyl, which is monosubstituted to trisubstituted by identical or different substituents from the series comprising hydroxyl, halogen, nitro, tetrazolyl, trifluoromethoxy, difluoromethoxy, trifluoromethyl, difluoro-methyl, cyano, carboxy, straight-chain or branched alkyl, alkylthio, alkoxy, alkoxycarbonyl or acyl each having up to 8 carbon atoms or by a group of formula —NR$^{17}$R$^{18}$, —(O)$_a$—SO$_2$—R$^{19}$ or —SO$_2$—NR$^{20}$R$^{21}$ in which a denotes a number 0 or 1, R$^{17}$ and R$^{18}$ have the meaning shown above for R$^{11}$ and R$^{12}$ and are identical to the latter or different from the latter, or R$^{17}$ denotes hydrogen and R$^{18}$ denotes straight-chain or branched acyl having up to 6 carbon atoms and R$^{19}$ has the above mentioned meaning of R$^{14}$ and is identical to the latter or different from the latter.

R$^{20}$ and R$^{21}$ have the above mentioned meaning of R$^{11}$ and R$^{12}$ and are identical to the latter or different from the latter and salts thereof.

The benzofuranyl- and -thiophenyl-alkanecarboxylic acids derivatives according to the invention can also be present in the form of their salts. In general, salts with organic or inorganic bases or acids may be mentioned here.

Physiologically acceptable salts are preferred in the context of the present invention. Physiologically acceptable salts of the benzofuranyl- and -thiophenyl-alkanecarboxylic acids derivatives can be metal or ammonium salts of the substances according to the invention, which contain a free carboxylic group. Those which are particularly preferred are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.

Physiologically acceptable salts can also be salts of the compounds according to the invention with inorganic or organic acids. Preferred salts here are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, ethanesulphonic acid, benzenesulphonic acid, toluenesulphonic acid or naphthalenedisulphonic acid.

The compounds according to the invention can exist in stereoisomeric forms which either behave as image and mirror image (enantiomers), or which do not behave as image and mirror image (diastereomers). The invention relates both to the antipodes and to the racemate forms, as well as the diastereomer mixtures. The racemate forms, like the diastereomers, can be separated into the stereoisomerically uniform constituents in a known manner.

Hydroxyl protective group in the context of the above-mentioned definition in general represents a protective group from the series comprising: trimethylsilyl, tert.butyl-dimethylsilyl, benzyl, 4-nitrobenzyl, 4-methoxybenzyl, acetyl, tetrahydropyranyl and benzoyl.

Heterocycle in general represents a 5- to 7-membered, preferably 5- to 6-membered, saturated or unsaturated ring which can contain up to three oxygen, sulphur and/or nitrogen atoms as heteroatoms and to which further aromatic ring can be fused.

5- and 6-membered tings having an oxygen, sulphur and/or up to two nitrogen atoms are preferred, which may also be fused to benzene.

The following are mentioned as preferred: thienyl, furyl, pyrrolyl, pyridyl, pyrimidyl, pyrazinyl, pyridazinyl, quinolyl, isoquinolyl, quinazolyl, quinoxazolyl, cinnolyl, thiazolyl benzothiaazolyl, isothiazolyl, benzisothiazolyl, oxazolyl, benzoxazolyl, isoxazolyl, imidazolyl, benzimidazolyl, indolyl, morpholinyl, pyrrolidinyl, piperidyl or piperazinyl.

Preferred compounds of the general formula (I) are those in which

R$^1$ and R$^2$ are identical or different and represent hydrogen, fluorine, chlorine, bromine, nitro, trifluoromethyl or a group of a formula —OR$^4$, —SR$^5$ or —NR$^6$R$^7$, in which R$^6$ denotes hydrogen or straight-chain or branched alkyl having up to 3 carbon atoms, R$^4$, R$^5$ and R$^7$ are identical or different and denote cyclopropyl, cyclobutyl, cyclopentyl, cyclohexyl, chinolyl, pyridyl, imidazolyl, 1,3-thiazolyl or thienyl, which are optionally substituted by identical or different substituents from the series comprising fluorine, chlorine, bromine, iodine, cyano, nitro or by straight-chain or branched alkyl or alkoxycarbonyl each having up to 5 carbon atoms or denote a residue of formula

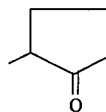 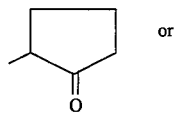

denote straight-chain or branched alkyl or alkenylen each having up to 6 carbon atoms, and each of which is optionally monosubstituted to trisubstituted by identical or different substituents from the series comprising trifluoromethyl, difluoromethyl, fluorine, chlorine, bromine, iodine, cyano, carboxy, hydroxy, straight-chain or branched alkoxy, alkoxycarbonyl or acyl each having up to 5 carbon atoms or by chinolyl, pyridyl, pyrazolyl, 1,3-thiadiazolyl, thienyl, imidazolyl or N-methyl-substituted imidazolyl, and to which an aromatic ring can be fused, or by a residue of formula

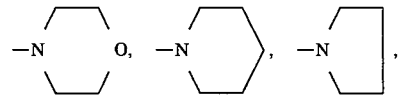

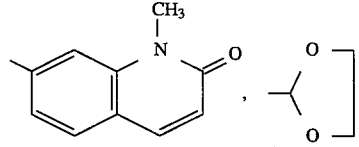

or by phenyl, where in, all rings are optionally monosubstituted to disubstituted by identical or different substituents from the series comprising nitro, fluorine, chlorine, bromine, iodine, carboxy or straight-chain or branched alkyl or alkoxycarbonyl each having up to 5 carbon atoms, or alkyl or alkenylen are substituted by a group of formula —CO—NR$^8$R$^9$ in which R$^8$ and R$^9$ are identical or different and denote phenyl, adamantyl, cyclopropyl, cyclopentyl, benzyl, formyl, hydrogen, straight-chain or branched alkyl or alkenyl each having up to 5 carbon atoms, which are optionally substituted by carboxy, hydroxy or straight-chain or branched alkoxycarbonyl up to 4 carbon atoms, or $R^8$ and $R^9$ together with the nitrogen atom form a morpholinyl, piperidinyl, piperazinyl or a pyrrolidinyl ring, or $R^4$ denotes acetyl, benzyl, tetrahydrofluorenyl, difluoromethyl or a group of a formula —$SO_2$—X, in which X denotes trifluoromethyl, phenyl or methyl, T represents an oxygen or sulfur atom V represents a straight-chain or branched alkylene or alkenylene chain each having 2 to 6 carbon atoms, W represents cyano, tetrazolyl or a group of a formula —CO—$R^{10}$, —CO—$NR^{11}R^{12}$, —$CONR^{13}$—$SO_2$—$R^{14}$ or $PO(OR^{15})(OR^{16})$, or a residue of the formula

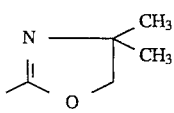

in which $R^{10}$ denotes hydroxyl, cyclopropyloxy, cyclopentyloxy, cyclohexyloxy or straight-chain or branched alkoxy having up to 6 carbon atoms, $R^{11}$, $R^{12}$ and $R^{13}$ are identical or different and denote hydrogen, phenyl or straight-chain or branched alkyl or acyl each having up to 4 carbon atoms and which are optionally substituted by hydroxyl, or $R^{11}$ denotes hydrogen and $R^{12}$ denotes hydroxyl or $R^{11}$ and $R^{12}$ together with the nitrogen atom form a pyrrolidinyl, piperidinyl ring or a morpholinyl, $R^{14}$ denotes straight-chain or branched alkyl having up to 5 carbon atoms, which is optionally substituted by phenyl or trifluoromethyl, or denotes phenyl, which is optionally substituted by substituents from the series comprising fluorine, chlorine, bromine, iodine, cyano, nitro or by straight-chain or branched alkyl having up to 4 carbon atoms, $R^{15}$ and $R^{16}$ are identical or different and represent hydrogen or straight-chain or branched alkyl having up to 6 carbon atoms, $R^3$ represents phenyl, which is monosubstituted to trisubstituted by identical or different substituents from the series comprising hydroxyl, fluorine, chlorine, bromine, iodine, nitro, trifluoromethoxy, difluoromethoxy, trifluoromethyl, difluoromethyl, cyano, carboxy, tetrazolyl, straight-chain or branched alkyl, alkylthio, alkoxy, alkoxycarbonyl or acyl each having up to 6 carbon atoms or by a group of formula —$NR^{17}R^{18}$, —$(O)_a$—$SO_2$—$R^{19}$ or —$SO_2NR^{20}R^{21}$, in which a denotes a number 0 or 1, $R^{17}$ and $R^{18}$ have the meaning shown above for $R^{11}$ and $R^{12}$ and are identical to the latter or different from the latter, or $R^{17}$ denotes hydrogen and $R^{18}$ denotes straight-chain or branched acyl having up to 6 carbon atoms and $R^{19}$ has the above mentioned meaning of $R^{14}$ and is identical to the latter or different from the latter, and $R^{20}$ and $R^{21}$ have the above mentioned meaning of $R^{11}$ and $R^{12}$ and are identical to the latter or different from the latter, and salts thereof.

Particularly preferred compounds of the general formula (I) are those in which $R^1$ denotes hydrogen, $R^2$ represents fluorine, chlorine, bromine, nitro, trifluoromethyl or a group of a formula —$OR^4$ or —$NR^6R^7$, in which $R^4$ denotes a group of a formula —$SO_2X$, in which X denotes trifluoromethyl, phenyl, methyl or difluoromethyl, or $R^4$ denotes hydrogen, tetrahydropyranyl, difluoromethyl, acetyl, benzyl, cyclopropyl, cyclobutyl, cyclopentyl, cyclohexyl, chinolyl, pyridyl, imidazolyl or thienyl, which are optionally substituted by identical or different substituents from the series comprising fluorine, chlorine, bromine, cyano, nitro or by straight-chain or branched alkyl or alkoxycarbonyl each having up to 4 carbon atoms or denotes a residue of the formula

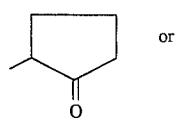

denotes straight-chain or branched alkyl or alkenylen each having up to 5 carbonatoms, and each of which is optionally monosubstituted to disubstituted by identical or different substituents from the series comprising trifluoromethyl, difluoromethyl, fluorine, chlorine, bromine, cyano, carboxy, hydroxy, straight-chain or branched alkoxy, alkoxycarbonyl or acyl each having up to 5 carbon atoms or by chinolyl, pyridyl, imidazolyl or N-methyl substituted imidazolyl, and to which an aromatic ring can be fused, or by a residue of formula

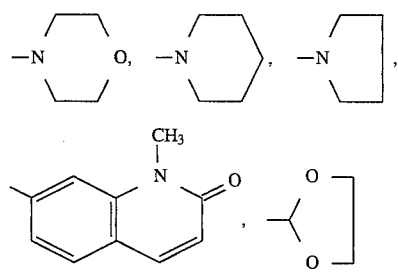

or by phenyl, wherein all rings are optionally monosubstituted to disubstituted by identical or different substituentes from the series comprising nitro, fluorine, chlorine, bromine, carboxy or straight-chain or branched alkyl or alkoxycarbonyl each having up to 4 carbon atoms, or alkyl or alkenylen are substituted by a group of formula —CO—$NR^8R^9$ in which $R^8$ and $R^9$ are identical or different and denote phenyl, benzyl, adamantyl, cyclopropyl, cyclopentyl, formyl, hydrogen, straight-chain or branched alkyl or alkenyl each having up to 5 carbon atoms, which are optionally hydroxy, substituted by carboxy, hydroxy or straight-chain or branched alkoxycarbonyl up to 3 carbon atoms or $R^8$ and $R^9$ together with the nitrogen atom form a morpholinyl, piperidinyl, piperazinyl or a pyrrolidinyl ring, $R^6$ denotes hydrogen, methyl or ethyl, $R^7$ denotes hydrogen, methyl or ethyl, T represents an oxygen or sulfur atom V represents a straight-chain or branched alkylene or alkenylene chain each having 2 to 5 carbon atoms, W represents cyano, tetrazolyl or a group of a formula —CO—$R^{10}$, —CO—$NR^{11}R^{12}$, —$CONR^{13}$—$SO_2$—$R^{14}$ or $PO(OR^{15})(OR^{16})$ or a residue of the formula

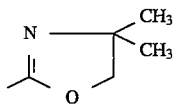

in which $R^{10}$ denotes hydroxyl, cyclopropyloxy, cyclopentyloxy, cyclohexyloxy or straight-chain or branched alkoxy having up to 5 carbon atoms, $R^{11}$, $R^{12}$ and $R^{13}$ are identical or different and denote phenyl, hydrogen, straight-chain or branched alkyl or acyl each having up to 4 carbon atoms and which are optionally substituted by hydroxyl, or $R^{11}$ denotes hydrogen and $R^{12}$ denotes hydroxyl or $R^{11}$ and $R^{12}$ together with the nitrogen atom form a pyrrolidinyl, piperidinyl or morpholinyl ring, $R^{14}$ denotes straight-chain or branched alkyl having up to 4 carbon atoms, which is optionally substituted by phenyl or trifluoromethyl, or denotes phenyl, which is optionally substituted by substituents from the series comprising fluorine, chlorine, bromine, cyano, nitro or by a straight-chain or branched alkyl having up to 3 carbon atoms, $R^{15}$ and $R^{16}$ are identical or different and represent hydrogen or straight-chain or branched alkyl having up to 5 carbon atoms, $R^3$ represents phenyl, which is monosubstituted to trisubstituted by identical or different substituents from the series comprising hydroxyl, fluorine, chlorine, bromine, nitro, tetrazolyl, trifluoromethyl, difluoromethyl, difluoromethoxy, trifluoromethoxy, cyano, carboxy, straight-chain or branched alkyl, alkylthio, alkoxy, alkoxycarbonyl or acyl each having up to 5 carbon atoms or by a group of formula —$NR^{17}R^{18}$, —$(O)_aSO_2$—$R^{19}$ or —$SO_2$—$NR^{20}R^{21}$, in which a denotes a number 0 or 1, $R^{17}$ and $R^{18}$ have the meaning shown above for $R^{11}$ and $R^{12}$ and are identical to the latter or different from the latter, or $R^{17}$ denotes hydrogen and $R^{18}$ denotes straight-chain or branched acyl having up to 5 carbon atoms and $R^{19}$ has the abovementioned meaning of $R^{14}$ and is identical to the latter or different from the latter, $R^{20}$ and $R^{21}$ have the above mentioned meaning of $R^{11}$ and $R^{12}$ and are identical to the latter or different from the latter, and salts thereof.

Processes for the preparation of the compounds of the general formula (I) have additionally been found, characterised in that

[A] compounds of the general formula (II)

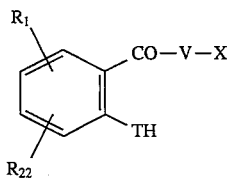

in which $R^1$, T, W and V have the abovementioned meaning $R^{22}$ represents a group of formula —$OR^{4'}$ in which $R^{4'}$ has the abovementioned meaning of $R^4$, but does not represent hydrogen, are reacted with compounds of the general formula (III)

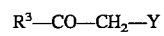

in which $R^3$ has the abovementioned meaning and

Y represents a typical leaving group such as, for example, chlorine, bromine, iodine, tosylate or mesylate, preferably bromine, in inert solvents and in the presence of a base under cyclisation by customary methods or '[B] in the case, in which V represents alkenyl, compounds of the general formula (IV)

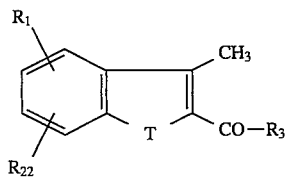

in which $R^1$, $R^3$, T and $R^{22}$ have the abovementioned meaning, first are converted by reaction with N-bromosuccinimide, in inert solvents and in the presence of a catalyst to the compounds of the general formula (V)

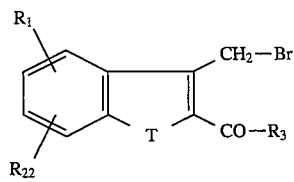

in which $R^1$, $R^3$, T and $R^{22}$ have the abovementioned meaning, and then by subsequent hydrolysis to compounds of the general formula (VI)

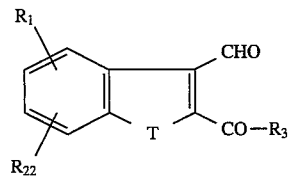

in which $R^1$, $R^3$, $R^{22}$ have the abovementioned meaning, which in a last step are reacted with compounds of the general formula (VII)

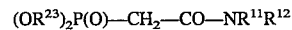

in which $R^{11}$ and $R^{12}$ have the abovementioned meaning, $R^{23}$ represents $C_1$–$C_4$-alkyl in inert solvents and in the presence of a base, and in the case of the free hydroxyl functions ($R^4$=H) the protective groups are removed by a customary method, and in the case of the acids ($R^{10}$=OH), the esters are hydrolysed, and in the case of the variation of the esters ($R^{10}\neq$OH) the acids are esterified with the appropriate alcohols in the presence of a catalyst according to a customary method, and in the case of the amides and sulfonamides ($R^4$/$R^5$/$R^7$=—$CONR^8R^9$/W=$CONR^{11}R^{12}$/—$CONR^{13}$—$SO_2R^{14}$), using amines of the formula (VIII) or sulfonamines of the formula (IX)

HN—$R^{24}R^{25}$      (VIII)

H—$NR^{13}$—$SO_2R^{14}$      (IX)

in which $R^{24}$ and $R^{25}$ have the abovementioned meaning of $R^8$, $R^9$, $R^{11}$ and $R^{12}$ and $R^{13}$ and $R^{14}$ have the abovementioned meaning, starting from the esters directly or starting from the free carboxylic acids, if appropriate in the presence of above and/or an auxiliary, an amidation or sulfonamidation follows.

The process according to the invention can be illustrated by way of example by the following equations:

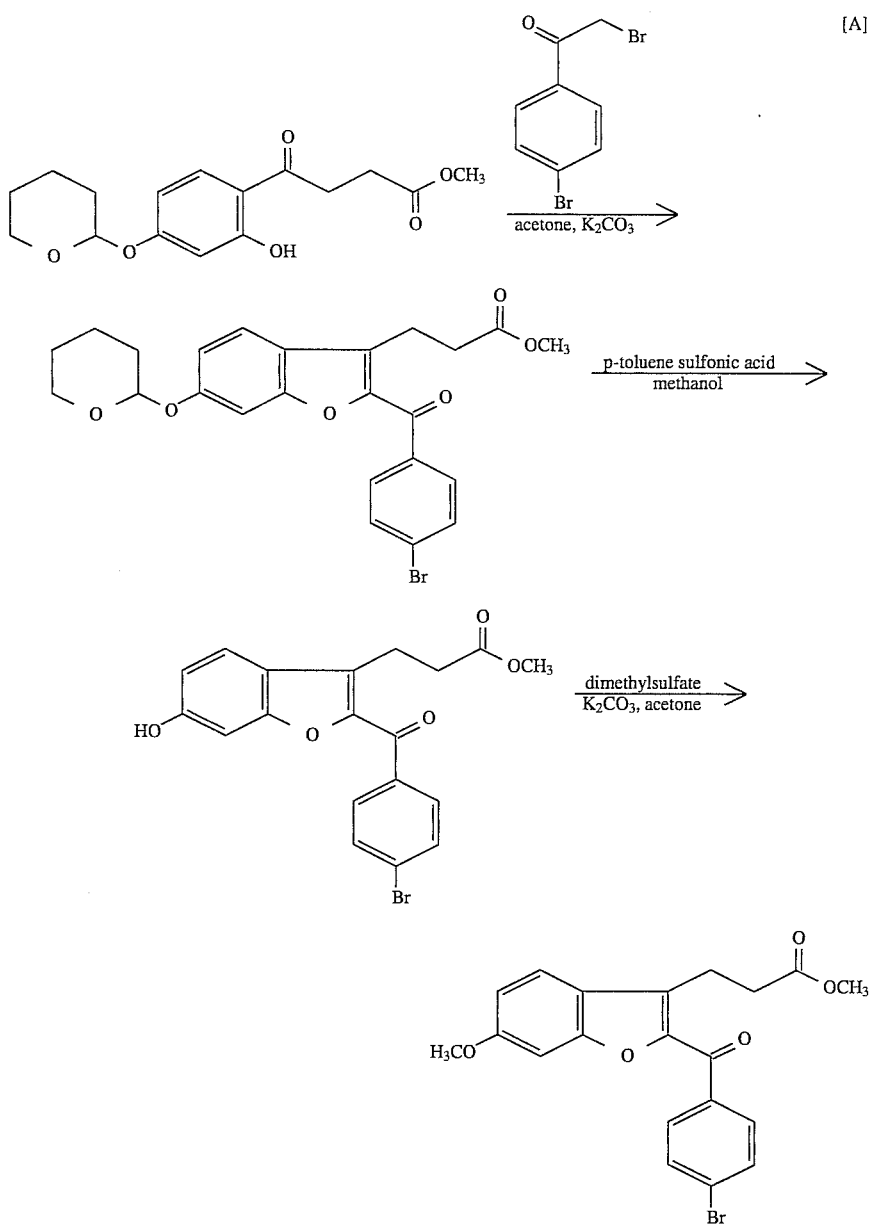

-continued

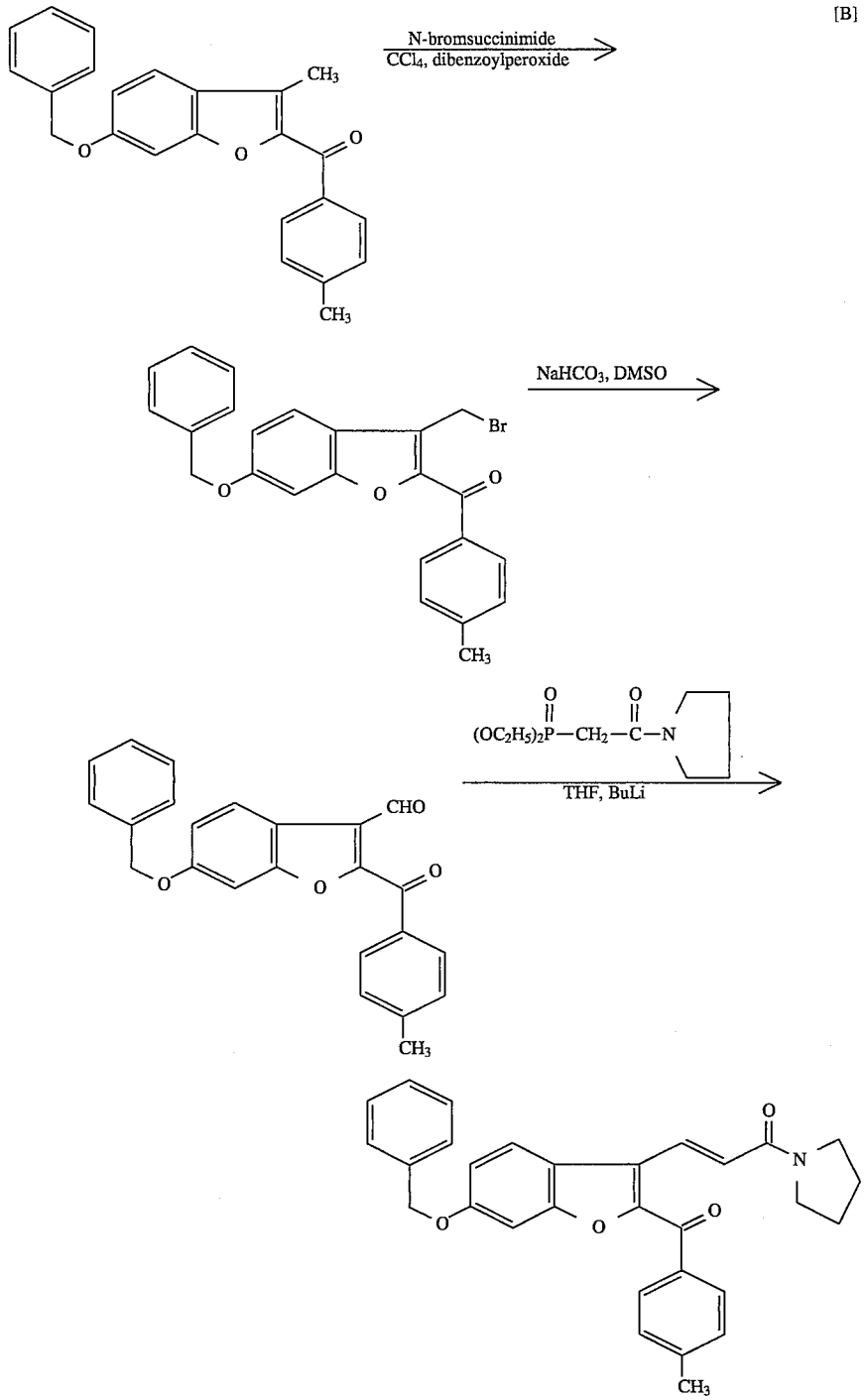

Suitable solvents are generally customary organic solvents which do not change under the reaction conditions. These preferably include ethers such as diethyl ether, dioxane, tetrahydrofurane or glycol dimethyl ether, acetone, dimethylsulfoxide, dimethylformamide, N-methylpyrrolidone, pyridyl, methylethyl- or methylisobutyl ketone.

Suitable bases am generally inorganic or organic bases. These preferably include alkali metal hydroxides such as, for example, sodium hydroxide, sodium hydrogencarbonate or potassium hydroxide, alkaline earth metal hydroxides such as, for example, barium hydroxide, alkali metal carbonates such as sodium carbonate, potassium carbonate, alkaline earth metal carbonates such as calcium carbonate, or alkaline metal oder alkaline earth metal alkoxides such as sodium methoxide or potassium methoxide, sodium ethoxide or potassium ethoxide or potassium tert.butoxide, or organic amines (trialkyl($C_1$-$C_6$)amines) such as triethylamine, or heterocycles such as 1,4-diazabicyclo[2.2.2]octane (DABCO), 1,8-diazabicyclo[5.4.0]-undec-7-ene (DBU), or amides such as sodium amides, lithium butyl amide or butyllithium, pyridine or methylpiperidine. It is also possible to employ alkali metals, such as sodium or its hydrides such as sodium hydride, as bases. Potassium carbonate, butyllithium and sodium hydrogencarbonate are prefered.

The base is employed in an amount from 1 mol to 10 mol, preferably from 1.0 mol to 2.1 mol, relative to 1 mol of the compounds of the general formula (III).

The reactions in general proceed in a temperature range from −70° C. to +100° C., preferably from −70° C. to +80° C. and at normal pressure.

The cyclisation in general proceeds in a temperature range from +30° C. to +180° C., preferably from +60° C. to +120° C. and at normal pressure.

The process according to the invention is in general carded out at normal pressure. However, it is also possible to carry out the process at elevated pressure or at reduced pressure (for example in a range from 0.5 to 5 bar).

Suitable solvents for the bromination are halogenohydrocarbons such as dichloromethane, trichloromethane, tetrachloromethane, dichloroethylene, trichloroethylene or chlorbenzene. Carbon tetrachloride is preferred for the bromination with N-bromsuccinimide, dichloromethane for the bromination with boron tribromide and glacial acetic acid for the bromination with hydrobromic acid.

Suitable catalysts for bromination are generally radical generators such as, for example, dibenzoyl peroxide or azobis-isobutyronitrile. Dibenzoyl peroxide is preferred.

The catalyst is employed in an amount from 0.001 mol to 0.2 mol, preferably form 0.1 mol to 0.05 mol, relative to 1 mol of the compounds of the general formula (IV).

The base is employed in an amount from 1 mol to 10 mol, preferably from 2.0 mol to 2.1 mol, relative each to 1 mol of the compounds of the general formula (VII).

Bromination is generally carried out in a temperature range from −30° C. to +150° C., preferably from −20° C. to +50° C.

Bromination is generally carded out at normal pressure. However, it is also possible to carry out bromination at elevated pressure or at reduced pressure (for example in a range from 0.5 to 5 bar).

The process is in general carded out in a temperature range from +10° C. to +150° C., preferably form +20° C. to +100° C.

The process is generally carded out at normal pressure. However, it is also possible to carry out it at elevated pressure or at reduced pressure (for example in a range from 0.5 to 5 bar).

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium methoxide, sodium ethoxide, potassium methoxide, potassium ethoxide or potassium tert.butoxide. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethyl-formamide, or dimethyl sulphoxide. Alcohols such as methanol, ethanol, propanol or isopropanol are particularly preferably used. It is also possible to employ mixtures of the solvents mentioned.

The hydrolysis can also be carried out with acids such as, for example, trifluoroacetic acid, acetic acid, hydrochloric acid, hydrobromic acid, methanesulphonic acid, sulphuric acid or perchloric acid, preferably with trifluoroacetic acid.

The hydrolysis is in general carded out in a temperature range from 0° C. to +180° C., preferably from +20° C. to +160° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mol, preferably from 1 to 1.5 mol, relative to 1 mol of the ester. Molar amounts of the reactants are particularly preferably used.

The amidation/sulphoamidation is in general carried out in one of the above-mentioned solvents, preferably in dichloromethane. It may optionally proceed, starting from the free carboxylic acid, via an activated stage, for example via the corresponding acid halides, which can be prepared from the corresponding acids by reaction with thionyl chloride, phosphorus trichloride, phosphorus pentachloride, phosphorus tribromide or oxalyl chloride. Preferably, the activated stages are prepared from the corresponding acids using dicyclohexylcarbodiimide, N-(3-dimethylaminopropyl)-N'-ethylcarbodiimide hydrochloride or carbonyldiimidazole and reacted in situ with the sulphonamides.

The amidation and the sulphoamidation are in general carried out in a temperature range from −20° C. to +80° C., preferably from −10° C. to +30° C. and at normal pressure.

In addition to the abovementioned bases, suitable bases for these reactions are preferably triethylamine and/or dimethylaminopyridine, DBU or DABCO.

The base is employed in an amount from 0.5 mol to 10 mol/l, preferably from 1 mol to 2 mol, relative to 1 mol of the appropriate ester or acid.

Acid-binding agents which can be employed for the sulphoamidation are alkali metal or alkaline earth metal carbonates such as sodium carbonate, potassium carbonate, alkali metal or alkaline earth metal hydroxides such as, for example, sodium hydroxide or potassium hydroxide, or organic bases such as pyridine, triethylamine, N-methylpiperidine, or bicyclic amidines such as 1,5-diazabicyclo-[3.4.0]-non-5-ene (DBN) or 1,5-diazabicyclo[3.4.0]undec-5-ene (DBU). Potassium carbonate is preferred.

Suitable dehydrating reagents are carbodiimides such as, for example, diisopropylcarbodiimide, dicyclohexylcarbodiimide or N-(3-dimethylaminopropyl)-N-'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxy-tri(dimethylamino)phosphonium hexafluorophosphate or diphenyl phosphoramidate or methanesulphonyl chloride, if appropriate in the presence of bases such as triethylamine or N-ethylmorpholine or N-methylpiperidine or dicyclohexylcarbodiimide and N-hydroxysuccinimide.

The acid-binding agents and dehydrating reagents are in general employed in an amount from 0.5 to 3 mol, preferably from 1 mol to 1.5 mol, relative to 1 mol of the corresponding carboxylic acids.

The compounds of the general formula (II) and (III) are known or can be prepared by published methods.

The compound of the general formula (IV) are known in some cases and, for example, can be prepared by reacting compounds of the general formula (X)

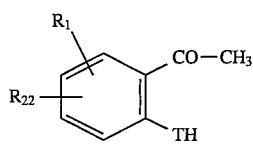

in which

R¹, T and R²² have the abovementioned meaning, with compounds of the general formula (III) in one of the abovementioned solvents and bases, preferably acetone and potassium carbonate.

The base is employed in an amount from 1 mol to 10 mol, preferably from 1.0 mol to 2.1 mol, relative to 1 mol of the compounds of the general formula (X)

The reactions in general proceed in a temperature range from +30° C. to +100° C., preferably from +40° C. to +80° C. and at normal pressure.

The compounds of the general formula (VIII), (IX) and (X) are known.

The compounds of the general formulas (V) and (VI) are known in some cases and can be prepared by the abovementioned processes.

The compounds of the general formula (VII) are known in some cases and can be prepared by customary methods.

The compounds according to the invention specifically inhibit the production of superoxide by polymorphonuclear leucocytes (PMN) without impairing other cell functions such as degranulation or aggregation. The inhibition was mediated by the elevation of cellular cAMP due to inhibition of the type IV phosphodiesterase responsible for its degradation They can therefore be employed in medicaments for controlling acute and chronic inflammatory processes.

The compounds according to the invention are preferably suitable for the treatment and prevention of acute and chronic inflammations of the airways, such as emphysema, alveolitis, shock lung, asthma, bronchitis, arteriosclerosis, arthrosis, inflammations of the gastro-intestinal tract and myocarditis. The compounds according to the invention are additionally suitable for reducing the damage to infarct tissue after reoxygenation. In this case the simultaneous administration of allopurinol to inhibit xanthine oxidase is of advantage. Combination therapy with superoxide dismutase is also of use.

TEST DESCRIPTION

1. Preparation of human PMN

Blood was taken from healthy subjects by venous puncture and neutrophils were purified by dextran sedimentation and resuspended in the buffered medium.

2. Inhibition of FMLP-stimulated production of superoxide racidal anions.

Neutrophils ($2.5 \times 10^5$ ml$^{-1}$) were mixed with cytochrome C (1.2 mg/ml) in the wells of a microtitre plate. Compounds according to the invention were added in dimethyl sulphoxide (DMSO). Compound concentration ranged from 2.5 nM to 10 μM, the DMSO concentration was 0.1% v/v in all wells. After addition of cytochalasin b (5 μg×ml$^{-1}$) the plate was incubated for 5 min at 37° C. Neutrophils were then stimulated by addition of $4 \times 10^{-8}$ M FMLP and superoxide generation measured as superoxide dismutase inhibitable reduction of cytochrome C by monitoring the OD$_{550}$ in a Thermomax microtitre plate spectrophotometer. Initial rates were calculated using a Softmax kinetic calculation programme. Blank wells contained 200 units of superoxide dismutase.

The inhibition of superoxide production was calculated as follows:

$$\left[ 1 - \frac{((Rx - Rb))}{((Ro - Rb))} \right] * 100$$

Rx=Rate of the well containing the compound according to the invention.

Ro=Rate in the control well.

Rb=Rate in the superoxide dismutase containing blank well.

3. Measurement of PMN cyclic AMP concentration

The compounds according to the invention were incubated with $3.7 \times 10^6$ PMN for 5 min at 37° C. before addition of $4 \times 10^{-8}$ M FMLP. After 6 min protein was precipitated by the addition of 1% v/v conc. HCl in 96% v/v ethanol containing 0.1 mM EDTA. After centrifugation the ethanolic extracts were evaporated to dryness under N$_2$ and resuspended in 50 mM Tris/HCl pH 7.4 containing 4 mM EDTA. The cyclic AMP concentration in the extracts was determined using a cyclic AMP binding protein assay supplied by Amersham International plc. Cyclic AMP concentrations were expressed as percentage of vehicle containing control incubations.

| Example No. | % elevation of [cAMP] at 1 μM (control 100) |
|---|---|
| 30 | 394 |

4. Assay of PMN phosphodiesterase

PMN suspensions ($10^7$ cells/ml) were sonicated for $6 \times 10$ sec on ice. Aliquots (100 μl) were incubated for 5 min at 37° C. with the compounds according to the invention or vehicle before the addition of $^3$H-cAMP (1 mM and 200 nCi per incubation). After 20 min the reaction was stopped by heating at 100° C. for 45 seconds. After cooling 100 mg of 5'-nucleotidase was added to each tube and the samples incubated for 15 min at 37° C. The conversion to $^3$H-adenosine was determined by ion-exchange chromatography on Dowex AG-1x (chloride form) followed by liquid scintillation counting. Percentage inhibition was determined by comparison to vehicle containing controls.

5. Effect of intravenously administered compounds on the FMLP-induced skin oedama of guinea pigs.

Guinea-pigs (600–800 g) were anaesthetized with pentobarbitone sodium (40 mg/kg, i.p.) and injected (i.V.) with a 0.5 ml mixture of pentamine sky blue (5% W/V) and $^{125}$I-HSA (1 μl/animal). 10 minutes later 3 intradermal injections of FMLP (10 μg/site), 1 injection of histamine (1 μg/site) and 1 injection of vehicle (100 μl of 0.2% DMSO V/V in Hanks Buffered salt solution) were made on the left hand side of the animal (preinjection sites). 5 minutes later the drug (1 ml/kg) or the vehicle (50% PEG 400 V/V in distilled water, 1 ml/kg) was administered (i.V.). 10 minutes later an identical pattern of intradermal injections was made on the opposite flank of the animal (post-injection sites). These responses were allowed to develop for 15 minutes before the animal was sacrificed and a blood sample taken.

Skin sites and plasma samples were counted for 1 minute on a gamma counter and the degree of oedema calculated as μl plasma/skin site. Statistical analysis was done by a paired t-test on the mean of the 3 pre-injection site values of μl plasma obtained for FMLP/animal. The percentage inhibition of drug or vehicle was calculated as follows $$X\% = \left(1 - \frac{\overline{X} \, \mu l \text{ plasma (post-injection site)}}{\overline{X} \, \mu l \text{ plasma (pre-injection site)}}\right) \times 100$$

| Example No. | % inhibition | (mg/kg) |
|---|---|---|
| 30 | 40.0 | (1) |

6. Effect of orally administered compounds on the FMLP-induced skin oedema of guinea-pigs in vivo-Test's p.o.

Guinea-pits (600–800 g) were fasted overnight and orally treated with vehicle (1% Tylose w/v at 5 ml/kg) or drug (10 mg/kg; 2 mg/ml in 1% Tylose at 5 ml/kg) 40 minutes later the animals were anasthetized with pentobarbitone sodium (40 mg/kg; i.p.) and 0.6 ml of a mixture of pontamine sky blue (5% w/v) and $^{125}$I-HSA (1 µci/animal) was injected (i.V.). 90 minutes after oral pretreatment FMLP (50 µg/site) was injected (i.d.) at 4 different sites, histamine (1 µg/site) and vehicle (100 µl, 1% DMSO v/v in Hanks buffered salt solution) were both injected (i.d.) at 2 different sites.

The responses were allowed to develop for 30 minutes before the animal was sacrificed and a blood sample taken.

Skin sites and plasma samples were counted for 1 minute on a gamma counter. The degree of oedema was calculated as µl plasma/skin site.

Statistical analysis was carried out by a Mann-Whitney U-test on the mean of the 4 values of µl Plasma obtained for FMLP/animal.

| Example No. | % inhibition | (mg/kg) |
|---|---|---|
| 30 | 46 | (25) |

The new active compounds can be converted in a known manner into the customary formulations, such as tablets, coated tablets, pills, granules, aerosols, syrups, emulsions, suspensions and solutions, using inert, nontoxic, pharmaceutically suitable excipients or solvents. In this connection, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can be used as auxiliary solvents if appropriate.

Administration is carded out in a customary manner, preferably orally or parenterally, in particular perlingually or intravenously.

In the case of parenteral administration, solutions of the active compound can be employed using suitable liquid vehicles.

In general, it has proved advantageous on intravenous administration to administer amounts from about 0.001 to 10 mg/kg, preferably about 0.01 to 5 mg/kg of body weight to achieve effective results, and on oral administration the dosage is about 0.01 to 25 mg/kg, preferably 0.1 to 10 mg/kg of body weight.

In spite of this, it may be necessary to depart from the amounts mentioned, in particular depending on the body weight or the type of application route, on individual behaviour towards the medicament, the manner of its formulation and the time or interval at which administration takes place. Thus, in some cases it may be sufficient to manage with less than the abovementioned minimum mount, while in other cases the upper limit mentioned must be exceeded. In the case of administration of relatively large amounts, it is advisable to divide these into several individual doses over the course of the day.

Solvents
I petrolether: ethylacetate 6:1
II petrolether: ethylacetate 5:1
III petrolether: ethylacetate 5:2
IV dichlormethane: methanol 95:5
V dichlormethane: methanol 9:1
VI dichlormethane
DMF dimethylformamide
Starting compounds

EXAMPLE I

2'-Hydroxy-3-oxo-4'-[tetrahydro-2H-pyran-2-yl)oxy]benzenebutanoic acid methylester

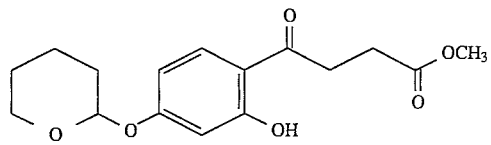

20.0 g (0,089 mol) 2',4'-Dihydroxy-3-oxo-benzenebutanoic acid methylester were dissolved in 200 ml dichloromethane/tetrahydrofuran (95:5) and 9.2 ml (0.1 mol) 3,4-dihydro-2H-pyran and 10 mg p-toluenesulfonic acid were added successively. The suspension was stirred at room temperature for 1 hour. 400 ml of a NaHCO$_3$ solution were added, the organic layer separated and washed three times with water. The organic phase was dried using Na$_2$SO$_4$ and concentrated in vacuo. The residue was recrystallised from diethylether.

Yield: 13.4 g (49% of theory) R$_f$=0,55, I

EXAMPLE II

4-Benzyloxy-2-hydroxyacetophenone

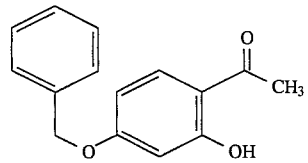

Equivalent amounts, 152.15 (1.0 mol) of 2,4-dihydroxy-acetophenone and 118.9 ml (1.0 mol) of benzylbromide were dissolved in 1.2 l acetone, 138 g potassium carbonate were added, and the mixture was stirred under reflux for 5 hours. Subsequently it was filtered off, the mother liquor was concentrated in vacuo and the residue recrystallised from diethylether. Yield: 197 g (81%) R$_f$=0.82, III

EXAMPLE III

6-Benzyloxy-3-methyl-2-(4-methylbenzoyl)benzo[b]furan

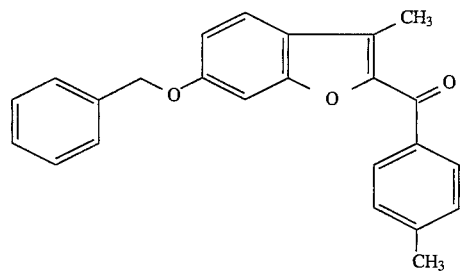

Equivalent amounts, 137.7 g (0,47 mol) 4-benzyloxy-2-hydroxy-acetophenone and 100 g (0,47 mol) ω-bromo-4-methylacetophenone were stirred under reflux for 12 h in 700 ml acetone in the presence of 65 g K$_2$CO$_3$. The mixture was filtered off, the solvent removed in vacuo and the residue recrystallised form diethylether.

Yield: 94 g (56%) R$_f$=0.63, II

EXAMPLE IV

6-Benzyloxy-3-bromo-methyl-2-(4-methylbenzoyl)benzo[b]furan

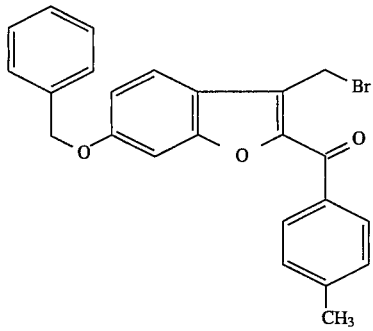

39.1 g (0.11 mol) of the compound from example III were dissolved in 500 ml carbon tetrachloride, 21.5 g (0.12 mol) of N-bromosuccinimide were added and the mixture was treated with 0.3 g dibenzoyl peroxide and heated to reflux for 12 hours. The mixture was filtered while hot, the solvent was distilled off in vacuo and the residue was purified by chromatography.

Yield: 19.4 g (41%) R$_f$=0.8, VI

EXAMPLE V and VI

6-Benzyloxy-2-(4-methylbenzoyl)-3-benzofuran-carboxaldehyde (V)

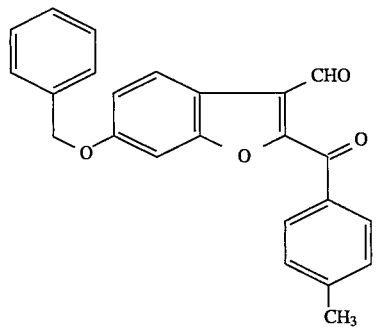

10.4 g NaHCO$_3$ in 60 ml DMSO were heated under argon to 150° C. 7.0 g (16 mmol) of 6-benzyloxy-3-bromo-methyl-2-(4-methylbenzoyl)benzo[b]furan, dissolved in 60 ml DMSO, were added within 1 min. After 15 min at 150° C. the mixture was poured onto ice and subsequently extraceted three times with ethylacetate/diethylether (1:1). The organic phase was washed twice with H$_2$O, once with a NaCl solution and dried over MgSO$_4$. The solvent was removed in vacuo and the residue purified by chromatography.

Yield: 5.4 g (91%) R$_f$=0.74, VI

By adding the benzylbromide (example IV) in a solidee form the 6-benzyloxy-3-hydroxymethyl-2-(4-methylbenzoyl)benzo[b]furan (VI) was isolated in changing yields.

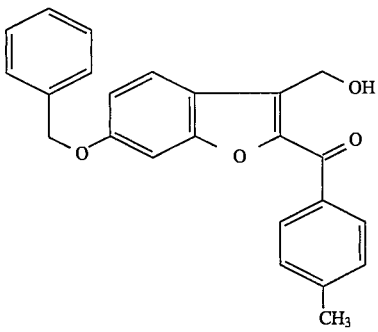

R$_f$: 0.17, II

EXAMPLE VII

Methyl 2'-hydroxy-3-oxo-5'-[(tetrahydro-2H-pyran-2-yl)oxy]benzene butanoate

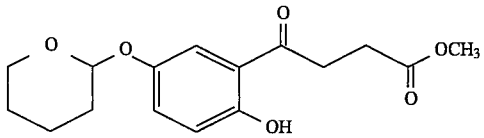

The compound has prepared in analogy to the procedure of Example I.

Yield: 56% R$_f$=0.58.

PREPARATION EXAMPLES

EXAMPLE I 2-(4-Bromo-benzoyl)-6-[(tetrahydro-2H-pyran-2-yl)oxy]-3-benzofuranpropanoic acid methylester

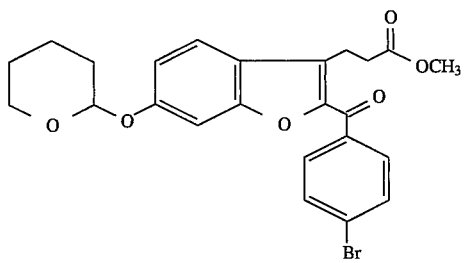

Equivalent amounts, 1.5 g (4.9 mmol) of 2'-Hydroxy-3-oxo-4'-[(tetrahydro-2H-pyran-2-yl)oxy]benzenebutanoic acid, methylester and 1,35 g (4.9 mmol) of ω-bromo-4-bromoacetophenone were dissolved in 50 ml acetone and 1,35 g (9.7 mmol) of potassium carbonate were added. The suspension was heated under reflux for 16 hours. The mixture was filtered, the solvent was distilled off in vacuo and the residue was taken up in ethylacetate. The organic phase was washed three times with water, one time with a NaCl solution, dried over Na$_2$SO$_4$ and concentrated in vacuo. The residue was further purified by chromatography (silica gel 60).

Yield: 1.54 g (65.1%) R$_f$=0.53, I

The compounds shown in Tables 1 and 2 are prepared in analogy to the procedure of Example 1:

TABLE 1

| Ex.-No. | A | D | E | L | Solvent | $R_f$* | Yield (% of theory) |
|---|---|---|---|---|---|---|---|
| 2 | H | H | $NO_2$ | H | | 0.72, III | 29 |
| 3 | H | H | $OCH_3$ | H | | 0.48, II | 50 |
| 4 | H | H | Cl | H | DMF | 0,45, II | 85 |
| 5 | H | H | F | H | | 0,63, II | 48 |
| 6 | H | H | $CF_3$ | H | | 0,65, II | 20 |
| 7 | H | H | CN | H | DMF | 0.45, III | 52 |
| 8 | H | H | $OCHF_2$ | H | DMF | 0,32, II | 44 |
| 9 | H | $NO_2$ | H | H | DMF | 0,49, III | 48 |
| 10 | H | CN | H | H | | 0.48, III | 30 |
| 11 | H | CN | $NH_2$ | H | | 0,38, III | 22 |
| 12 | $OCH_3$ | H | H | $OCH_3$ | | 0,49, III | 53 |
| 13 | H | Cl | $NHCOCH_3$ | H | | 0,30, III | 50 |
| 14 | H | Br | H | H | | 0,65, III | 53 |
| 15 | H | H | $CH_3$ | H | | 0,67, II | 55 |
| 16 | H | Cl | H | H | | 0.70, III | 46 |
| 17 | H | H | $COOCH_3$ | H | | 0,56, III | 60 |
| 18 | H | Cl | $NH_2$ | Cl | | 0.53, III | 38 |
| 19 | Cl | H | Cl | H | | 0,50. II | 75 |

TABLE 2

| Ex.-No. | A | D | E | a | Solvent | $R_f$* | Yield (% of theory) |
|---|---|---|---|---|---|---|---|
| 20 | H | H | $CH_3$ | 2 | | 0.57, VI | 16 |
| 21 | H | H | F | 2 | | 0.66, II | 23 |
| 22 | H | H | $CH_3$ | 3 | | 0,68, VI | quanti. |
| 23 | H | $NO_2$ | H | 3 | MIBK | 0,68, II | 32 |
| 24 | H | H | $NO_2$ | 2 | MIBK | 0.41, II | 7 |
| 25 | H | $NO_2$ | H | 2 | MIBK | 0,65, II | 63 |
| 26 | H | H | CN | 2 | | 0,39, III | 62 |

MIBK = methylisobutylketone

EXAMPLE 27

2-(4-Bromo-benzoyl)-6-hydroxy-3-benzofuranpropanoic acid methylester

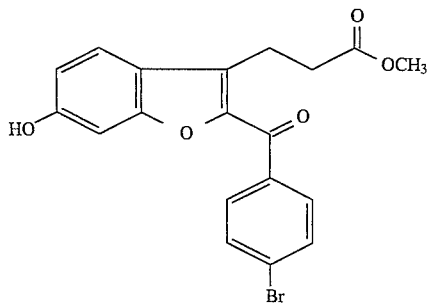

4.2 g (8.64 mmol) of 2-(4-Bromo-benzoyl)-6-[(tetrahydro-2H-pyran-2-yl)oxy-3-benzofuranpropanoic acid methylester were dissolved in 100 ml methanol and 10 mg p-toluene-sulfonic acid were added. The suspension was stirred at r.t. for 2 hours. The solvent was distilled off, the residue solved in ethylacetate and washed two times with water, once with a $NaHCO_3$ solution and once with a NaCl solution. The organic layer was dried using $Na_2SO_4$, concentrated in vacuo and the residue was further purified by chromatography (silica gel 60).

Yield: 3.0 g (86%) $R_f$: 0.30, III

The compounds shown in Table 3 are prepared in analogy to the procedure of Example 27:

TABLE 3

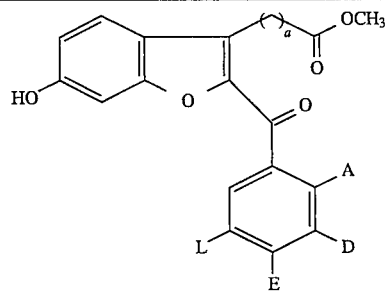

| Ex.-No. | A | D | E | L | a | $R_f$* | Yield (% of theory) |
|---|---|---|---|---|---|---|---|
| 28 | H | H | NO$_2$ | H | 2 | 0.27, III | 80 |
| 29 | H | H | OCH$_3$ | H | 2 | 0.46, III | 85 |
| 30 | H | H | Cl | H | 2 | 0,31, III | 50 |
| 31 | H | H | F | H | 2 | 0,10, II | 89 |
| 32 | H | H | CF$_3$ | H | 2 | 0,14, II | 61 |
| 33 | H | H | CN | H | 2 | 0.73, V | 94 |
| 34 | H | H | OCHF$_2$ | H | 2 | 0,08, II | 96 |
| 35 | H | NO$_2$ | H | H | 2 | 0,21, III | 70 |
| 36 | H | CN | H | H | 2 | 0.10, II | 70 |
| 37 | H | CN | NH$_2$ | H | 2 | 0,08, III | 81 |
| 38 | OCH$_3$ | H | H | OCH$_3$ | 2 | 0.17, III | 96 |
| 39 | H | Cl | NHCOCH$_3$ | H | 2 | 0,77, V | 82 |
| 40 | H | Br | H | H | 2 | 0,37, III | 65 |
| 41 | H | H | CH$_3$ | H | 2 | 0.09, II | 63 |
| 42 | H | Cl | H | H | 2 | 0.43, III | 10 |
| 43 | H | H | COOCH$_3$ | H | 2 | 0.24, III | 37 |
| 44 | H | Cl | NH$_2$ | Cl | 2 | 0.32, III | 87 |
| 45 | H | CH$_3$ | CH$_3$ | H | 2 | 0.09, II | 90 |
| 46 | H | CH$_3$ | H | H | 2 | 0.10, II | 95 |
| 47 | H | H | CH$_2$CH$_3$ | H | 2 | 0.10, III | 85 |
| 48 | H | H | CH$_3$ | H | 4 | 0.45, IV | 90 |
| 49 | H | Cl | Cl | H | 2 | 0.20, III | 89 |
| 50 | Cl | H | Cl | H | 2 | 0,35, III | 45 |

EXAMPLE 51

6-Hydroxy-2-(4-methyl-benzoyl)-3-benzofuranpropanoic acid

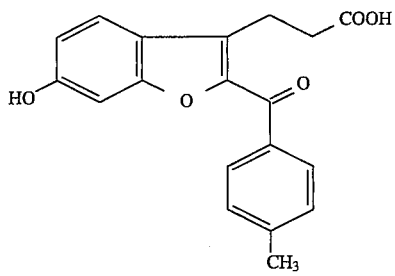

1.5 g (4.4 mmol) of the compound from example 41 were dissolved in 50 ml methanol/tetrahydrofuran (1:1) and 5.5 ml of a 2N NaOH solution were added. The mixture was stirred at r.t. for 24 hours, dissolved in water and acidified with 1N hydrochloric acid. The precipitate was filtered off, washed several times with water and dried in vacuo.

Yield: 1.4 g (97%) $R_f$: 0.29, V

The compounds shown in Table 4 are prepared in analogy to the procedure of example 51:

TABLE 4

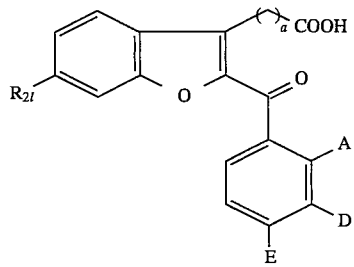

| Ex.-No. | A | D | E | L | a | $R_f$* | Yield (% of theory) |
|---|---|---|---|---|---|---|---|
| 52 | H | CH$_3$ | H | —OH | 2 | 0.27, V | quant. |
| 53 | H | CH$_3$ | CH$_3$ | —OH | 2 | 0.13, IV | quant. |
| 54 | H | H | CH$_2$CH$_3$ | —OH | 2 | 0,13, IV | quant. |
| 55 | H | H | CH$_3$ | —OCH$_2$—C$_6$H$_5$ | 2 | 0,54, V | 94 |
| 56 | H | H | CH$_3$ | —Cl | 2 | 0,37, V | 57 |
| 57 | H | H | OCH$_3$ | —OH | 2 | 0,41, V | quant. |
| 58 | H | H | Cl | —OH | 2 | 0.55, V | 95 |
| 59 | H | H | F | —OH | 2 | 0,50, V | 90 |
| 60 | H | H | Br | —OH | 2 | 0.55, V | quant. |
| 61 | H | H | CF$_3$ | —OCH$_3$ | 2 | 0,56, IV | 94 |
| 62 | H | H | CN | —OCH$_3$ | 2 | 0,54, IV | 72 |
| 63 | H | H | Br | —OH | 4 | 0.20, IV | 95 |
| 64 | H | H | CH$_3$ | —OH | 4 | 0.58, V | 94 |

EXAMPLE 65

2-(4-Cyano-benzoyl)-6-methoxy3-benzofuran-propanoic acid methylester

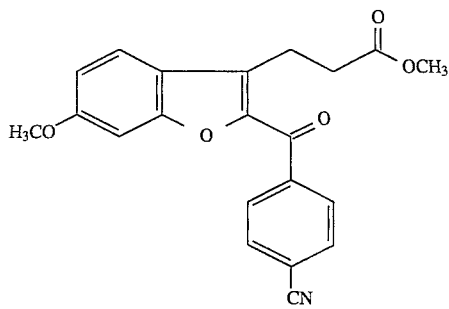

0.2 g (0,57 mol) of the compound from example 33 were dissolved in 10 ml acetone and subsequently 100 mg potassium carbonate and 0.054 ml (0.57 mmol) dimethylsulfate were added. The mixture was heated under reflux for 1 hour, the solvent removed in vacuo and the residue washed several times with diethylether. The product was further purified, if appropriate, by chromatography.

Yield: 0.13 g (63%) $R_f$=0.60, III

The compounds shown in Table 5 are prepared in analogy to the procedure of Example 65:

TABLE 5

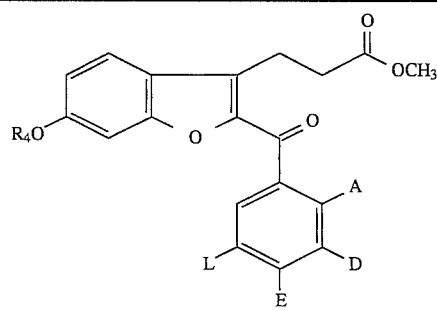

| Ex.-No. | A | D | E | L | $R^4$ | $R_f$* | Yield (% of theory) | Solvent | M.P. (°C.) |
|---|---|---|---|---|---|---|---|---|---|
| 66 | H | H | Cl | H | CH₃ | 0.70, III | 95 | | |
| 67 | H | H | Br | H | CH₃ | 0.69, III | quant. | | |
| 68 | H | H | CF₃ | H | CH₃ | 0.70, III | quant. | | |
| 69 | H | CN | H | H | CH₃ | 0.49, III | quant. | | |
| 70 | OCH₃ | H | H | OCH₃ | CH₃ | 0.35, III | 94 | | |
| 71 | H | CN | NH₂ | H | CH₃ | 0.18, III | 71 | | |
| 72 | H | NO₂ | H | H | CH₃ | 0.47, III | 62 | | |
| 73 | H | Cl | H | H | CH₃ | 0,65, III | quant. | | |
| 74 | H | Cl | NH₂ | Cl | CH₃ | 0,74, III | quant. | | |
| 75 | Cl | H | Cl | H | CH₃ | 0,65, III | 95 | | |
| 76 | H | H | CN | H | CH₂—CO—OCH₃ | 0.23, III | 91 | | |
| 77 | OCH₃ | H | H | OCH₃ | —CH₂—CO—OCH₃ | 0.29, III | 84 | DMF | 50 |
| 78 | H | CN | NH₂ | H | —CH₂—CO—OCH₃ | 0.09, III | 56 | DMF | 50 |
| 79 | H | Br | H | H | —CH₂—CO—OCH₃ | 0.49, III | quant. | DMF | 50 |
| 80 | H | Br | H | H | —CH₂—CO—OC₂H₅ | 0.59, III | 85 | DMF | 50 |
| 81 | H | Br | H | H | —CH₂—CO—CH₃ | 0.44, III | 92 | | |
| 82 | H | H | NO₂ | H | —CH₂—CO—OCH₃ | 0.35, III | quant. | | |
| 83 | H | H | NO₂ | H | —CH₂—CO—OC₂H₅ | 0.48, III | quant. | | |
| 84 | H | NO₂ | H | H | —CH₂—CO—OCH₃ | 0.23, III | 85 | | |
| 85 | H | NO₂ | H | H | —C₅H₉ | 0.65, III | 79 | | |
| 86 | H | Cl | H | H | —CH₂—CO—OCH₃ | 0.39, III | 88 | | |
| 87 | H | Cl | H | H | —C₅H₉ | 0.58, II | quant. | | |
| 88 | H | H | CH₃ | H | —CH₃ | 0.25, II | 77 | | |
| 89 | H | H | CH₃ | H | —CH₂—CO—CH₃ | | 78 | | 57 |
| 90 | H | H | CH₃ | H | —CH₂—CO—C₄H₉ | | 41 | | 53 |
| 91 | H | H | CH₃ | H | —C₅H₉ | | 63 | | 64 |
| 92 | H | H | CH₃ | H | —CH₂—CO—OCH₃ | 0.07, II | 68 | | |
| 93 | H | H | CH₃ | H | —CH₂—C₆H₅ | 0.60, VI | 80 | | |
| 94 | H | H | OCH₃ | H | —CH₂—C₆H₅ | 0.40, IV | 85 | | |
| 95 | H | Cl | NH—CO—CH₃ | H | —CH₂—CO—OCH₃ | 0.10, III | 70 | | |
| 96 | H | Cl | Cl | H | —CH₂—CO—OCH₃ | 0.20, II | 89 | DMF | |
| 97 | H | Cl | Cl | H | —CH₂—CO—OC₂H₅ | 0.28, II | quant. | DMF | |
| 98 | H | H | CH₃ | H | —H₂C—(2-quinolinyl) | | 81 | DMF | 98 |

TABLE 5-continued

[Structure diagram: benzofuran with R4O- substituent, -CH2CH2COOCH3 chain, and carbonyl-phenyl group with substituents A, D, E, L]

| Ex.-No. | A | D | E | L | R⁴ | Yield (% of theory) | Solvent | M.P. (°C.) |
|---|---|---|---|---|---|---|---|---|
| 99 | H | H | CH₃ | H | [1-methyl-6-methylene-2-oxo-1,2-dihydroquinoline group: -H₂C-(6-position of N-methyl quinolin-2(1H)-one)] | 61 | DMF | 126 |
| 100 | H | H | CH₃ | H | [6-methyl-3-nitro-2-pyridyl-methyl: -H₂C-(pyridine with NO₂)] | 59 | DMF | 102 |
| 101 | H | H | CH₃ | H | —CH₂—CO—C₂H₅ | 81 | DMF | 89 |
| 102 | H | H | Cl | H | —CH₂—CO—OCH₃ | 79 | DMF | 83 |
| 103 | H | H | Cl | H | —C₅H₉ | 58 | DMF | 48 |
| 104 | H | H | Cl | H | —CH₂—CO—CH₃ | 50 | DMF | 75 |
| 105 | H | H | CH₃ | H | —C₂H₅ | 86 | | 65 |
| 106 | H | H | Cl | H | —C₂H₅ | 84 | DMF | 59 |
| 107 | H | H | Cl | H | —H₂C—(quinolin-2-yl) | 70 | DMF | 108 |

| Ex.-No. | A | D | E | L | R⁴ | Yield (% of theory) | Solvent | M.P. (°C.) | R_f* |
|---|---|---|---|---|---|---|---|---|---|
| 108 | H | H | CH₃ | H | —CH₂—CO—OC₂H₅ | 62 | | 115 | |
| 109 | H | H | Cl | H | —CH₂—CO—OC₂H₅ | 45 | DMF | 72 | |
| 110 | H | H | Cl | H | —CH₂—CO—C₂H₅ | 84 | DMF | 86 | 0.39, III |
| 111 | H | H | Cl | H | [2-methyl-cyclopentanone group] | 30 | DMF | | 0.44, III |
| 112 | H | H | Cl | H | —C₃H₆—COOCH₃ | 56 | DMF | 56 | 0.43, III |
| 113 | H | H | Cl | H | —CH₂—C(=CH₂)—COOCH₃ | 81 | DMF | 96 | 0.28, II |
| 114 | H | H | Cl | H | —CH₂—C(=CH₂)—COOH | 57 | DMF | 145 | 0.29, IV |
| 115 | H | H | Cl | H | —CH₂—CH=CH—COOCH₃ | 47 | DMF | 62 | 0.44, III |
| 116 | H | H | Cl | H | —CHC(CN)(CH₃) | 45 | | DMF | 0.55, III |
| 117 | H | H | Cl | H | —H₂C—C(=O)NH₂ | 60 | 166 | DMF | 0.44, IV |

EXAMPLE 118

6-Methoxy-2-(4-tetrazolyl-benzoyl)-3-benzofuran-propanoic acid methylester

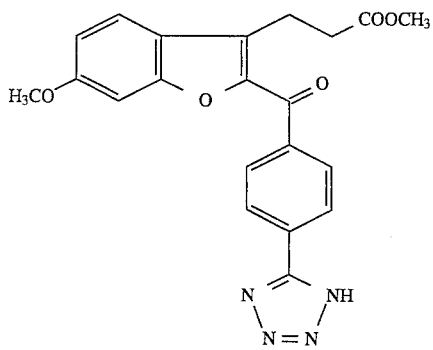

0.95 g (2.62 mmol) of the compound from example 65 were dissolved in 15 ml DMF, 0.85 g (13.1 mmol) sodium azide and 1.80 g (13.1 mmol) triethylamine hydrochloride were added and the mixture was heated under reflux for 24 h. After cooling at room temperature the mixture was diluted with diethylether and subsequently washed three times with $H_2SO_4$ (1M), three times with water and 2 times with a NaCl solution. The organic phase was dried using $MgSO_4$, the solvent was removed in vacuo and the residue purified by chromatography using dichloromethane/methanol (9:1).

Yield: 0.79 g (74%) $R_f$:0.09, V

EXAMPLE 119

6-chloro-2-(4-tetrazolyl-benzoyl)-3-benzofuran-propanoic acid methylester

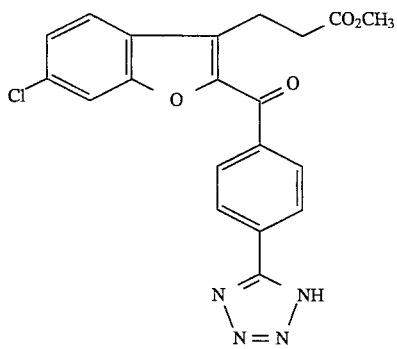

The title compound can be prepared in analogy to the procedure of Example 118.

EXAMPLE 120

6-Hydroxy-2-(4-methyl-benzoyl)-3-benzofuran-propanoic acid ethylester

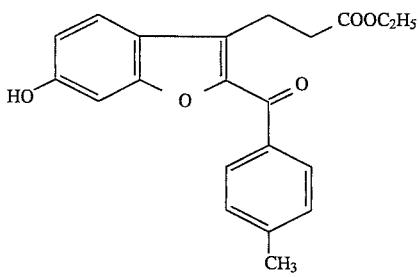

0.4 g (1.23 mmol) of the acid from example 51 were dissolved in 25 ml trichloromethane and 1.2 g p-toluenesulfonic acid and 5 ml ethanol were added. The mixture was stirred under reflux for 24 h using a water separator. Subsequently the mixture was washed two times with water, dried over $Na_2SO_4$ and concentrated in vacuo.

Yield: quant. $R_f$: 0.57, IV

The compounds shown in Table 6 are prepared in analogy to the procedure of Example 120:

TABLE 6

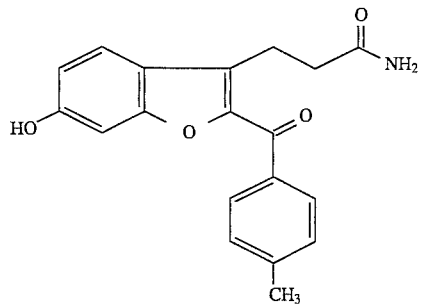

| Ex.-No. | A | D | E | R | $R_f$* | Yield (% of theory) |
|---|---|---|---|---|---|---|
| 121 | H | $CH_3$ | $CH_3$ | $-CH_2CH_3$ | 0.64, V | 98 |
| 122 | H | $CH_3$ | $CH_3$ | $-CH(CH_3)_2$ | 0.68, V | 89 |
| 123 | H | H | $CH_3$ | $-C_5H_9$ | 0.56, IV | quant. |

EXAMPLE 124

6-Hydroxy-2-(4-methyl-benzoyl)-3-benzofuranpropanamide 0.5 g (1.54 mmol) of the acid from example 51 were dissolved in 5 ml THF, 1.06 g (6.55 mmol) 1,1'-carbonyl-bis-1H-imidazole were added and the mixture was stirred at room temperature for 12 hours. Subsequently $NH_3$-gas was added for 2 hours using an inlet pipe. After one additional hour stirring at r.t. the solvent was distilled off in vacuo. The residue was taken up in ethylacetate and washed three times with water, one time with a $NaHCO_3$ solution and one time with a NaCl solution. The organic phase was dried using $MgSO_4$ and the solvent was removed in vacuo.

Yield: quant. $R_f$: 0.42, V

The compounds shown in Table 7 are prepared in analogy to the procedure of Example 124:

TABLE 7

[Structure: 6-hydroxy-2-(4-methyl-benzoyl)benzofuran with 3-CH2CH2C(O)R substituent]

| Ex.-No. | R | $R_f$* | Yield (% of theory) |
|---|---|---|---|
| 125 | —NH—CH₃ | 0.38, V | 97 |
| 126 | —N(CH₃)₂ | 0.34, V | 94 |

The compounds shown in Table 8 are prepared in analogy to the procedure of Example 65:

TABLE 8

[Structure: R4O-substituted benzofuran with 3-CH2CH2C(O)OCH3 and 2-(4-methyl-benzoyl) substituents]

| Ex.-No. | R⁴ | $R_f$* | Yield (% of theory) |
|---|---|---|---|
| 127 | —CH₃ | 0.21, II | 30 |
| 128 | —CH₂—C₆H₅ | 0.28, II | 40 |
| 129 | —CH₂—C₆H₄—pNO₂ | 0.13, II | 68 |
| 130 | —CH₂—C₆H₄—pCOOCH₃ | 0.14, II | 62 |
| 131 | —C₅H₉ | 0.34, II | 56 |

EXAMPLE 132

6-Benzyloxy-2-(4-methyl-benzoyl)-3-[3-oxo-3-(1-pyrrolidinyl)propenyl]benzo[b]-furan

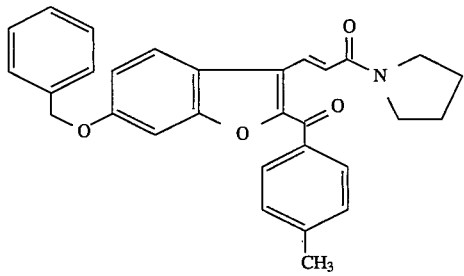

0.5 g (1.35 mmol) of the compound from example V were dissolved in 5 ml THF, cooled to 31 70° C. and 0.8 ml (2.0 mmol) of n-BuLi (2.5M solution in hexane) were added dropwise. Subsequently the mixture was stirred for 30 min. at 31 70° C. and 0.50 g (2.0 mmol) of O,O-diethyl-[2-oxo-2-(1-pyrrolidinyl)ethyl]phosphonacid ester, solved in 5 ml THF, were added dropwise. After stirring for 30 min. at 31 70° C. the cooling bath was removed. After warming to 0° C. 10 ml of a NH₄Cl solution were added. The mixture was extracted with ethylacetate and the organic phase was washed three times with water, one time with a NaCl solution and dried using MgSO₄. The solvent was distilled off and the residue purified by chromatography.

Yield: 0.45 g (72%) $R_f$: 0.51, IV

The compounds shown in Table 9 are prepared in analogy to the procedure of Example 132:

TABLE 9

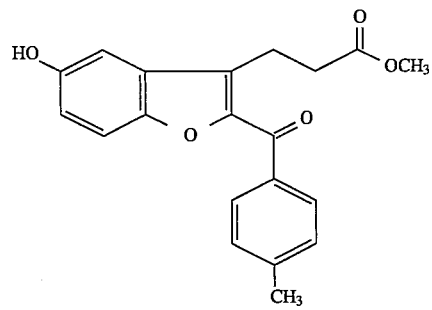

| Ex.-No. | E | $R_f$* | Yield (% of theory) |
|---|---|---|---|
| 133 | —COOCH₃ | 0.19, III | 60 |
| 134 | —NO₂ | 0.28, III | 65 |

EXAMPLE 135

Methyl 5-hydroxy-2-(4-methyl-benzoyl)-3-benzofuran-propionate

[Structure: 5-hydroxy benzofuran with 3-CH2CH2COOCH3 and 2-(4-methyl-benzoyl)]

The title compound is prepared according to the process A starting from the compound of example VII.

TABLE 10

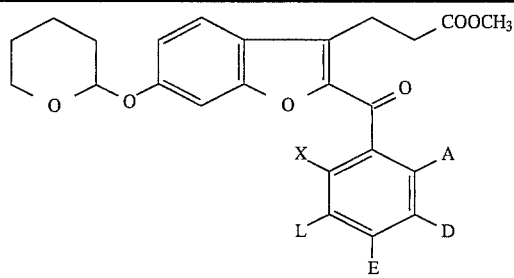

| Ex. No. | A | D | E | L | X | Solvent | $R_f$ | Yield (% of theory) |
|---|---|---|---|---|---|---|---|---|
| 136 | H | Cl | Cl | H | H | DMF | 0.43, II | 40 |
| 137 | CH$_3$ | —NH—CO—CH$_3$ | CH$_3$ | H | H | DMF | 0.48, IV | 39 |
| 138 | H | CH$_3$ | Cl | H | H | DMF | 0.42, II | 38 |
| 139 | F | H | H | H | F | DMF | 0.20, III | 38 |
| 140 | F | H | F | H | H | DMF | 0.45, II | 20 |
| 141 | CH$_3$ | —NH—CO—CH$_3$ | Cl | H | H | DMF | 0.60, IV | 34 |
| 142 | H | H | —SO$_2$—CH$_3$ | H | H | DMF | 0.26, III | 59 |
| 143 | H | H | —SCH$_3$ | H | H | DMF | 0.38, II | 73 |
| 144 | H | H | —O—SO$_2$—CH$_3$ | H | H | DMF | 0.24, III | 75 |
| 145 | H | H | —SO$_2$—N(morpholino) | H | H | DMF | 0.37, III | 60 |
| 146 | H | NO$_2$ | Cl | H | H | DMF | 0.66, III | 13 |
| 147 | OCH$_3$ | H | H | H | OCH$_3$ | DMF | 0.15, II | 70 |

TABLE 11

| Ex. No. | A | D | E | L | X | $R_f$ | Yield (% of theory) |
|---|---|---|---|---|---|---|---|
| 148 | CH$_3$ | —NH—CO—CH$_3$ | CH$_3$ | H | H | 0.45 V | 54 |
| 149 | H | CH$_3$ | Cl | H | H | 0.15 II | 94 |
| 150 | F | H | F | H | H | 0.40 III | 81 |
| 151 | CH$_3$ | —NH—CO—CH$_3$ | Cl | H | H | 0.47 IV | 88 |
| 152 | H | H | —SO$_2$—CH$_3$ | H | H | 0.57 IV | 71 |
| 153 | H | H | —S—CH$_3$ | H | H | 0.12 III | 82 |
| 154 | H | H | —O—SO$_2$—CH$_3$ | H | H | 0.46 IV | 83 |
| 155 | H | H | —SO$_2$—N(morpholino) | H | H | 0.43 IV | 97 |
| 156 | H | —NO$_2$ | Cl | H | H | 0.65 IV | 71 |
| 157 | H | H | (tetrazolyl) | H | H | 0.02 V | 17 |

TABLE 11-continued

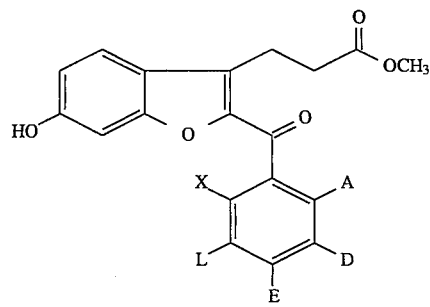

| Ex. No. | A | D | E | L | X | $R_f$ | Yield (% of theory) |
|---|---|---|---|---|---|---|---|
| 158 | F | H | H | H | F | 0.13 II | 96 |
| 159 | OCH$_3$ | H | H | H | —OCH$_3$ | 0.63 IV | 90 |

TABLE 12

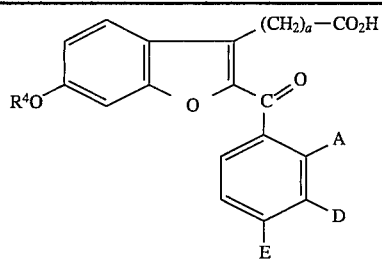

| Ex. No. | A | D | E | R$^4$ | a | $R_f$ | Yield (% of theory) |
|---|---|---|---|---|---|---|---|
| 160 | H | H | Cl | —CH$_2$—CO—NH$_2$ | 2 | 0.07 (IV) | 75 |
| 161 | H | H | Cl | —CH$_2$COOH | 2 | 0.1 (IV) | 95 |
| 162 | H | H | Cl | —CH$_2$CON⟨morpholino⟩ | 2 | | |
| 163 | H | H | Cl | —CH$_2$CON⟨piperidino⟩ | 2 | 0.33 (IV) | 64 |
| 164 | H | H | Cl | —CH$_2$CON⟨pyrrolidino⟩ | 2 | 0.35 (IV) | 66 |
| 165 | H | H | Cl | —CH$_2$CON(C$_2$H$_5$)$_2$ | 2 | 0.40 (IV) | 55 |
| 166 | H | H | Cl | —CH$_2$CON(CH$_3$)$_2$ | 2 | 0.41 (IV) | 11 |
| 167 | H | Cl | H | —CH$_2$CONH$_2$ | 2 | 0.08 (IV) | 86 |
| 168 | H | H | Br | —CH$_2$CONH$_2$ | 2 | 0.07 (IV) | 93 |
| 169 | H | H | Cl | —CH$_2$CONHCH$_2$CH(CH$_3$)$_2$ | 2 | 0.2 (IV) | 46 |
| 170 | H | H | Cl | —CH$_2$CONHCH$_2$CH=CH$_2$ | 2 | 0.1 (IV) | 90 |
| 171 | H | H | Cl | —CH$_2$CONHC$_3$H$_7$ | 2 | 0.1 (IV) | 88 |
| 172 | H | H | Cl | —CH$_2$CN | 2 | 0.15 (IV) | 80 |
| 173 | H | H | CH$_3$ | —CH$_2$CN | 2 | 0.16 (IV) | 90 |
| 174 | H | H | Cl | —CH$_2$CH$_2$OH | 2 | 0.1 (IV) | 85 |

TABLE 12-continued

[Structure: benzofuran with R⁴O substituent, (CH₂)ₐ-CO₂H group, and carbonyl linked to phenyl ring with A, D, E substituents]

| Ex. No. | A | D | E | R⁴ | a | R_f | Yield (% of theory) |
|---|---|---|---|---|---|---|---|
| 175 | H | H | Cl | -CH₂CH(O-CH₂-CH₂-O) (dioxolane) | 2 | 0.2 (IV) | 89 |

TABLE 13

[Structure: benzofuran with R⁴O substituent, -CH₂-CH₂-CO-OCH₃ chain, carbonyl linked to phenyl ring with A, D, E, L, X substituents]

| Ex. No. | A | D | E | L | X | R⁴ | R_f | Yield (% of theory) |
|---|---|---|---|---|---|---|---|---|
| 176 | H | Cl | NH₂ | Cl | H | -CH₂CO-OCH₃ | 0.48, III | quant. |
| 177 | H | Cl | NH₂ | Cl | H | -CH₂-CO-NH₂ | 0.45, V | 86 |
| 178 | CH₃ | -NH-CO-CH₃ | CH₃ | H | H | -CH₂-CO-OCH₃ | 0.58, V | quant. |
| 179 | CH₃ | -NH-CO-CH₃ | CH₃ | H | H | -CH₂-CO-NH₂ | 0.54, V | 84 |
| 180 | H | CH₃ | Cl | H | H | -CH₂-CO-OCH₃ | 0.58, III | quant. |
| 181 | H | CH₃ | Cl | H | H | -CH₂-CO-NH₂ | 0.60, V | 91 |
| 182 | H | Cl | NH₂ | Cl | H | -CH₃ | 0.71, III | quant. |
| 183 | F | H | H | H | F | -CH₂-CO-OCH₃ | 0.36, III | 95 |
| 184 | F | H | H | H | F | -CH₂-CO-NH₂ | 0.65, V | 98 |
| 185 | F | H | F | H | H | -CH₂-CO-OCH₃ | 0.19, III | 97 |
| 186 | F | H | F | H | H | -CH₂-CO-NH₂ | 0.53, IV | 92 |
| 187 | CH₃ | -NH-CO-CH₃ | Cl | H | H | -CH₂-CO-OCH₃ | 0.56, IV | 75 |
| 188 | CH₃ | -NH-CO-CH₃ | Cl | H | H | -CH₂-CO-NH₂ | 0.28, IV | 72 |
| 189 | H | H | -S-CH₃ | H | H | -CH₂-CO-OCH₃ | 0.17, III | 87 |
| 190 | H | H | -S-CH₃ | H | H | -CH₂-CO-NH₂ | 0.53, IV | quant. |
| 191 | H | H | -SO₂-CH₃ | H | H | -CH₂-CO-OCH₃ | 0.9, IV | 86 |
| 192 | H | H | -SO₂-CH₃ | H | H | -CH₂-CO-NH₂ | 0.32, IV | 67 |
| 193 | H | H | -O-SO₂-CH₃ | H | H | -CH₂-CO-OCH₃ | 0.79, IV | 88 |
| 194 | H | H | -O-SO₂-CH₃ | H | H | -CH₂-CO-NH₂ | 0.42, IV | 88 |
| 195 | H | H | -SO₂-N(morpholino) | H | H | -CH₂-CO-OCH₃ | 0.89, IV | 88 |
| 196 | H | H | -SO₂-N(morpholino) | H | H | -CH₂-CO-NH₂ | 0.46, IV | 89 |
| 197 | H | -NO₂ | Cl | H | H | -CH₂-CO-OCH₃ | 0.15, III | 69 |
| 198 | H | H | tetrazole (N-N=N-NH) | H | H | -CH₂-CO-NH₂- | 0.42, V | quant. |

TABLE 13-continued

[Structure: benzofuran with R4O substituent, methyl propanoate group, and carbonyl linked to phenyl ring bearing substituents A, D, E, L, X]

| Ex. No. | A | D | E | L | X | R$^4$ | R$_f$ | Yield (% of theory) |
|---|---|---|---|---|---|---|---|---|
| 199 | H | —CN | H | H | H | —CH$_2$—CO—OCH$_3$ | 0.22, III | quant. |
| 200 | —Cl | H | Cl | H | H | —CH$_2$—CO—OCH$_3$ | 0.25, II | 95 |
| 201 | H | H | [tetrazole: N—N / N—N—H] | H | H | —CH$_2$—CO—OCH$_3$ | 0.75, V | 35 |

TABLE 14

[Structure: benzofuran with R4O, CO$_2$CH$_3$ side chain, and CO linked to phenyl ring with substituents A, D, E, L]

| Ex. No. | A | D | E | L | R$^4$ | R$_f$ | Yield (% of theory) | m.p. °C. |
|---|---|---|---|---|---|---|---|---|
| 202 | H | H | Cl | H | —CH$_2$—C≡N | 0.5 (III) | 76 | 75 |
| 203 | H | H | Cl | H | —(CH$_2$)$_3$—C≡N | 0.32 (III) | 85 | 77 |
| 204 | H | H | CH$_3$ | H | —CH$_2$—C(=O)—NH$_2$ | 0.4 (IV) | 87 | 160 |
| 205 | H | H | NO$_2$ | H | —CH$_2$—C(=O)—NH$_2$ | 0.4 (IV) | 97 | 181 |
| 206 | H | H | CH$_3$ | H | —CH$_2$—C(=CH$_2$)—COOH | 0.6 (IV) | 66 | 123 |
| 207 | H | NO$_2$ | H | H | —CH$_2$—C(=O)—NH$_2$ | 0.15 (IV) | 88 | 181 |
| 208 | H | Br | H | H | —CH$_2$—C(=O)—NH$_2$ | 0.24 (IV) | 81 | 174 |
| 209 | H | CN | H | H | —CH$_2$—C(=O)—NH$_2$ | 0.17 (IV) | 87 | 203 |
| 210 | Cl | H | Cl | H | —CH$_2$—C(=O)—NH$_2$ | 0.46 (IV) | 48 | 161 |

TABLE 14-continued

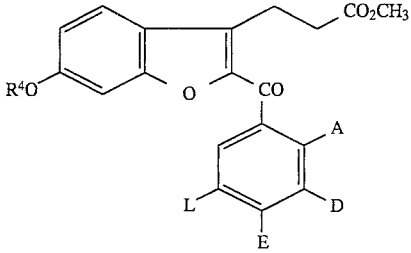

| Ex. No. | A | D | E | L | R⁴ | $R_f$ | Yield (% of theory) | m.p. °C. |
|---|---|---|---|---|---|---|---|---|
| 211 | H | H | CN | H | —CH₂—C(=O)—NH₂ | 0.47 (IV) | 85 | 206 |
| 212 | H | H | Cl | H | —CH₂—COOH | 0.52 (V) | 36 | |
| 213 | H | H | CH₃ | H | —CH₂—C≡N | 0.37 (III) | 96 | |
| 214 | H | H | Cl | H | —CH₂—(1-methylimidazol-2-yl) | 0.46 (IV) | quant. | |
| 215 | H | H | Cl | H | —SO₂CF₃ | 0.79 (III) | 96 | |
| 216 | H | H | CH₃ | H | —SO₂CF₃ | 0.75 (III) | 82 | |
| 217 | H | H | CH₃ | H | —CH₂—(1-methylimidazol-2-yl) | 0.44 (IV) | 90 | |
| 218 | H | H | Cl | H | —CF₂H | 0.34 (II) | 48 | |
| 219 | H | H | Cl | H | —CH₂CF₃ | 0.44 (II) | 20 | 96 |
| 220 | H | H | Cl | H | —CH₂CH₂—N(morpholino) | 0.4 (IV) | 89 | |
| 221 | H | H | Cl | H | —CH₂CH₂—N(pyrrolidino) | 0.23 (IV) | 79 | |
| 222 | H | H | Cl | H | —CH₂CH₂—N(piperidino) | 0.31 (IV) | 89 | |
| 223 | H | H | Cl | H | —CH₂—CO—N(morpholino) | 0.43 (IV) | 94 | 123–124 |
| 224 | H | H | Cl | H | —CH₂—CO—N(piperidino) | 0.71 (IV) | 96 | |
| 225 | H | Cl | H | H | —CH₂—CO—NH₂ | 0.37 (IV) | 78 | 185 |
| 226 | H | H | Br | H | —CH₂—CO—NH₂ | 0.46 (IV) | 72 | 160 |

TABLE 14-continued

[Structure: benzofuran with R⁴O- substituent, -CH₂CH₂CO₂CH₃ at 3-position, -CO-phenyl at 2-position; phenyl bearing A (ortho), D (meta), E (para), L (meta)]

| Ex. No. | A | D | E | L | R⁴ | $R_f$ | Yield (% of theory) | m.p. °C. |
|---|---|---|---|---|---|---|---|---|
| 227 | H | H | Cl | H | -CH₂-C(1,3-dioxolan-2-yl) | 0.15 (VI) | 30 | 114 |
| 228 | H | H | Cl | H | -CH₂CH₂Cl | 0.79 (III) | 16 | 224 |
| 229 | H | H | Cl | H | -CH₂CH₂OH | 0.21 (III) | 32 | 96 |
| 230 | H | H | Cl | H | -CH₂-C(=O)N(CH₃)((CH₂)₃CH₃) | 0.8 (IV) | 90 | |
| 231 | H | H | Cl | H | -CH₂-C(=O)N(C₂H₅)((CH₂)₃CH₃) | 0.8 (IV) | 96 | |
| 232 | H | H | Cl | H | -CH₂-C(=O)N(pyrrolidinyl) | 0.56 (IV) | 85 | 123–4 |
| 233 | H | H | Cl | H | -CH₂-C(=O)N(C₂H₅)₂ | 0.74 (IV) | 93 | |
| 234 | H | H | Cl | H | -CH₂-C(=O)N(CH₃)(CHO) | 0.84 (IV) | 10 | |
| 235 | H | H | Cl | H | -CH₂-C(=O)N(CH₃)₂ | 0.57 (IV) | 95 | 144–146 |
| 236 | H | H | Cl | H | -CH₂-C(=O)NHCH₂C₆H₅ | 0.84 (IV) | 64 | 126–129 |
| 237 | H | H | Cl | H | -CH₂-C(=O)N(C₃H₇)₂ | 0.91 (IV) | 96 | 99–101 |

TABLE 14-continued

[Structure: benzofuran with R4O substituent, CO2CH3 chain, and benzoyl group with A, D, E, L substituents]

| Ex. No. | A | D | E | L | R⁴ | R_f | Yield (% of theory) | m.p. °C. |
|---|---|---|---|---|---|---|---|---|
| 238 | H | H | Cl | H | —CH₂—C(=O)N(C₄H₉)₂ | 0.91 (IV) | 91 | |
| 239 | H | H | Cl | H | —CH₂—C(=O)N(i-Bu)H | 0.9 (IV) | 72 | 133–135 |
| 240 | H | H | Cl | H | —CH₂—C(=O)NCH₃H | 0.52 (IV) | 30 | 135–137 |
| 241 | H | H | Cl | H | —CH₂—C(=O)NCH₂—CH=CH₂H | 0.73 (IV) | 75 | 129 |
| 242 | H | H | Cl | H | —CH₂—C(=O)N—C₃H₇H | 0.64 (IV) | 61 | 121 |
| 243 | H | H | Cl | H | —COCH₃ | 0.27 (II) | 67 | |
| 244 | H | H | Cl | H | —CH₂CONHCH₂CO₂C₂H₅ | 0.4 (V) | 62 | 114–116 |
| 245 | H | H | CH₃ | H | cyclobutyl | 0.8 (III) | 10 | |
| 246 | H | H | Cl | H | CH₂CONHCH₂OH | 0.4 (III) | 22 | 128 |

The compounds shown in Table 15 are prepared in analogy to the procedure of Example 65

TABLE 15

[Structure: benzofuran with R4O, OCH3 ester chain, and p-methylbenzoyl group]

| Ex. No. | R⁴ | R_f | Yield (% of theory) |
|---|---|---|---|
| 247 | —CH₂—CO—OCH₃ | 0.71, IV | 74 |
| 248 | —CH₂—CO—OC₂H₅ | 0.72, IV | 78 |
| 249 | —CH₂—CO—NH₂ | 0.30, IV | 20 |

47

The compounds shown in Table 16 are prepared in analogy to the procedure of Example 132

TABLE 16

R₄O—[benzofuran]—CH=CH—CN with CO—phenyl—E substituent

| Ex. No. | R₄ | E | $R_f$ | Yield (% of theory) |
|---------|------|----|-------|---------------------|
| 250 | H₃C— | Cl | 0.42, II | 61 |

EXAMPLE 251

2-(4-Chloro-benzoyl)-6-methoxy-3-benzofuranpropionitril

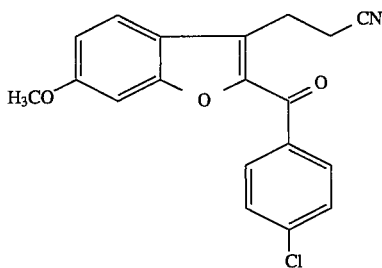

0.49 g (1.45 mmol) of the compound from example 250 was suspended in 10 ml methanol and hydrogenated for 1 hour at 3.5 bar and room temperature in the presence of 60 mg palladium-on-charcoal catalyst (5%). The catalyst was filtered off and the residue was evaporated. The product was further purified, if appropriate, by chromatography.

Yield: 71% $R_f$=0.40, II

EXAMPLE 252

2-(4-Chloro-benzoyl)-6-hydroxy-3-benzofuranpropionitril

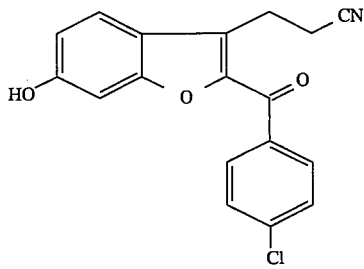

The title compound is prepared according to example 251.

48

EXAMPLE 253

(4-Chloro-phenyl)-{6-methoxy-3-[2-(2H-tetrazol-5-yl)-ethyl]-benzofuran-2-yl}-methanone

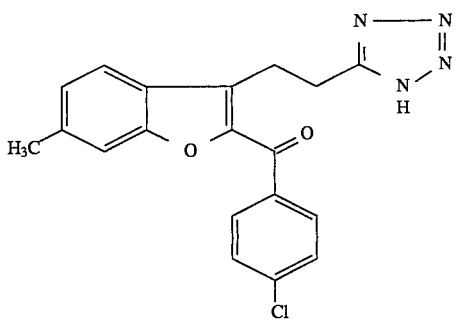

0.2 g (0.59 mmol) of the compound from example 251 were dissolved in 5 ml xylene and 0.17 ml (0.59 mmol) tributyltin chloride and 38.4 mg sodium azide were added. The resulting mixture was heated at 80° C. under argon atmosphere for 3 days. After the mixture was cooled to ambient temperature, it was added with stirring to 10 ml of ice-cold, dry methanol saturated with HCl gas. The mixture was stirred for 90 min before it was concentrated in vacuo. The residue was purified by chromatography.

Yield: 49% $R_f$: 0.02, V

EXAMPLE 254

3 -[2-(4-Chloro-benzoyl)-6-[(tetrahydro-2H-pyran-2-yl)oxy]-benzofuran-3-yl]-N-(2-hydroxy-1,1-dimethyl-ethyl)-propionamide

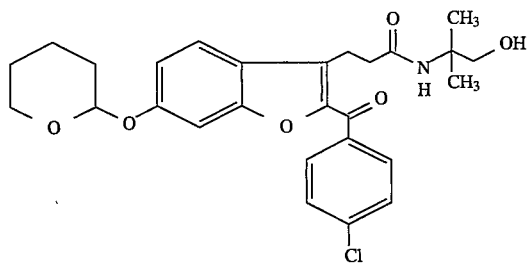

3.0 g (7.0 mmol) of the acid from example 4 were dissolved in a mixture of 10 ml acetonitrile/10 ml pyridine and 623 mg (7.0 mmol) 2-amino-2-methylpropanol, 2.9 ml (21.0 mmol) triethylamine and 2.03 ml (21.0 mmol) tetrachloromethane were added. 5.5 g (21.0 mmol) triphenylphosphin dissolved in a mixture of 10 ml acetonitril/10 ml pyridine were added dropwise. After stirring at room temperature for 12 h the mixture was diluted with water and extracted 3×with ethylacetate. The organic phase was washed with a NaCl solution, dried using MgSO₄ and the solvent was removed in vacuo. The residue was purified by chromatography using dichloromethane/methanol (9:1 ).

Yield: 2.42 g (72%) $R_f$: 0.64, V.

EXAMPLE 255

(4-Chloro-phenyl)-{3-[2-(4,4-dimethyl-4,5-dihydro-oxazol-2-yl)-ethyl]-6-hydroxybenzofuran-2-yl}-methanone

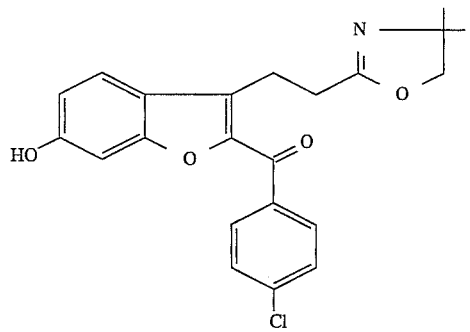

0.58 ml (8 mmol) thionylchloride were added dropwise under stirring to 1.0 g (2.0 mmol) of the compound from example 254. The mixture was stirred at room temperature for 12 hours and the excess thionylchloride was removed in vacuo. The residue was taken up in water and the pH of the solution was adjusted to pH=8 by adding a 1N sodium hydroxide solution. After extraction of the water phase 3×with ethylether and removing of the solvent in vacuo the residue was purified by column chromatography.

Yield: 0.7 g (85%) $R_f$: 0.70, V.

EXAMPLE 256

2-{2-(4-Chloro-benzoyl)-3-[2-(4,4-dimethyl-4,5-dihydro-oxazol-2-yl)-ethyl]-benzofuran-6-yloxy}-acetamide

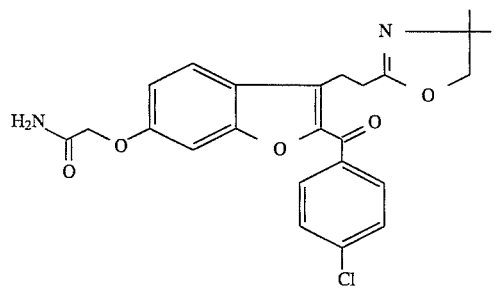

The title compound is prepared according to example 65.

The compounds shown in Table 17 are prepared by reaction of the carbon acids with NaOH.

TABLE 17

| Ex. No. | $R^4$ | A | D | E | $R_f$ | Yield (% of theory) |
|---|---|---|---|---|---|---|
| 257 | —CH$_2$CO—NH$_2$ | H | H | Cl | 0.1 (V) | 95 |
| 258 | —CH$_2$—CO—N(piperidinyl) | H | H | Cl | 0.2 (V) | 98 |
| 259 | —CH$_2$—CO—N(pyrrolidinyl) | H | H | Cl | 0.2 (V) | 97 |
| 260 | —CH$_2$—CO—N(C$_2$H$_5$)$_2$ | H | H | Cl | 0.15 (V) | 98 |

The compounds shown in Table 18 are prepared in analogy to the procedure of example 65.

TABLE 18

| Ex. No. | A | D | E | R⁴ | $R_f$ | Yield (% of theory) |
|---|---|---|---|---|---|---|
| 261 | H | H | CH₃ | —CH₂—C(=O)—NH—C₁₀H₁₅ | 0.58 (IV) | 57 |
| 262 | H | H | CH₃ | —CH₂—C(=O)—NH—cyclopropyl | 0.25 (IV) | 80 |
| 263 | H | H | CH₃ | —CH₂—C(=O)—N(piperidinyl) | 0.36 (IV) | 86 |
| 264 | H | H | CH₃ | —CH₂—C(=O)—NH—CH₂C(CH₃)₃ | 0.30 (IV) | 74 |
| 265 | H | H | CH₃ | —CH₂—C(=O)—NH—propyl | 0.33 (IV) | 74 |
| 266 | H | H | Br | —CH₂—C(=O)—NH—C₁₀H₁₅ | 0.5 (IV) | 86 |
| 267 | H | H | Br | —CH₂—C(=O)—NH—cyclopropyl | 0.28 (IV) | 75 |
| 268 | H | H | Br | —CH₂—C(=O)—N(piperidinyl) | 0.28 (IV) | 86 |

TABLE 18-continued
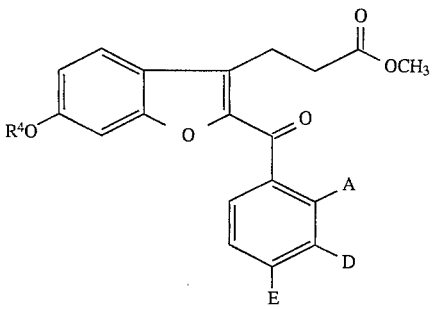
| Ex. No. | A | D | E | R⁴ | R_f | Yield (% of theory) |
|---|---|---|---|---|---|---|
| 269 | H | H | Br | 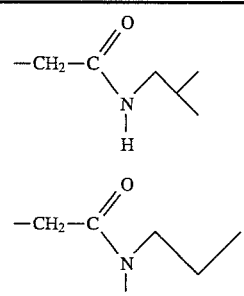 | 0.29 (IV) | 65 |
| 270 | H | H | Br | 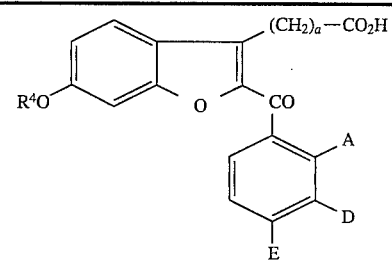 | 0.28 (IV) | 80 |
TABLE 19
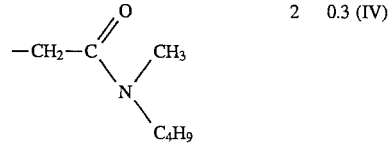
| Ex. No. | A | D | E | R⁴ | a | R_f | Yield (% of theory) |
|---|---|---|---|---|---|---|---|
| 271 | H | Cl | H | —OH | 2 | 0.2 (IV) | 83 |
| 272 | H | H | Cl | 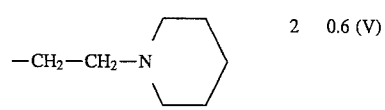 | 2 | 0.15 (IV) | 95 |
| 273 | H | H | Cl | 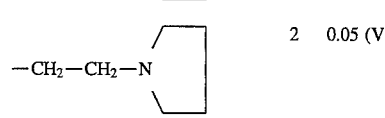 | 2 | 0.3 (IV) | 40 |
| 274 | H | H | Cl | —CH₂—CH₂—N(piperidine) | 2 | 0.6 (V) | 42 |
| 275 | H | H | Cl | —CH₂—CH₂—N(pyrrolidine) | 2 | 0.05 (V) | 20 |

TABLE 19-continued

| Ex. No. | A | D | E | R⁴ | a | $R_f$ | Yield (% of theory) |
|---|---|---|---|---|---|---|---|
| 276 | H | H | Cl | —CH₂—CH₂—N(morpholine) | 2 | 0.5 (IV) | 80 |
| 277 | H | H | Br | —CH₂—C(O)—NH—C₁₀H₁₅ | 2 | 0.42 (V) | 50 |
| 278 | H | H | Br | —CH₂—C(O)—NH—cyclopropyl | 2 | 0.23 (V) | 61 |
| 279 | H | H | Br | —CH₂—C(O)—piperidine | 2 | 0.29 (V) | 79 |
| 280 | H | H | Cl | —CH₂—C(O)—NH—isobutyl | 2 | 0.25 (V) | 67 |
| 281 | H | H | Br | —CH₂—C(O)—NH—propyl | 2 | 0.27 (V) | 85 |
| 282 | H | H | CH₃ | —CH₂—C(O)—NH—C₁₀H₁₅ | 2 | 0.54 (V) | 58 |
| 283 | H | H | CH₃ | —CH₂—C(O)—NH—cyclopropyl | 2 | 0.26 (V) | 88 |
| 284 | H | H | CH₃ | —CH₂—C(O)—piperidine | 2 | 0.44 (V) | 47 |

TABLE 19-continued

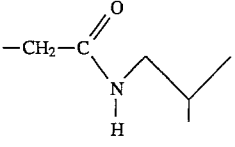

| Ex. No. | A | D | E | R⁴ | | a | $R_f$ | Yield (% of theory) |
|---|---|---|---|---|---|---|---|---|
| 285 | H | H | CH₃ | —CH₂—C(=O)NH—CH₂CH(CH₃)₂ | | 2 | 0.26 (V) | 85 |
| 286 | H | H | CH₃ | —CH₂—C(=O)NH—CH₂CH₂CH₃ | | 2 | 0.22 (V) | 74 |

The compounds shown in Table 20 were prepared in analogy to the procedure of Example 120.

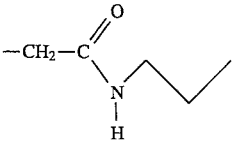

| Ex. No. | A | D | E | R¹⁰ | $R_f$ | Yield (% of theory) |
|---|---|---|---|---|---|---|
| 287 | H | H | Br | —O—C(CH₃)₃ | 0.2 (IV) | 40 |
| 288 | H | H | Br | —O—CH(CH₃)₂ | 0.22 (IV) | 43 |

EXAMPLE 289

2-[2-(4-Chloro-benzoyl)-3-(2-cyano-ethyl)-benzofuran-6-yl-oxy]-acetamide

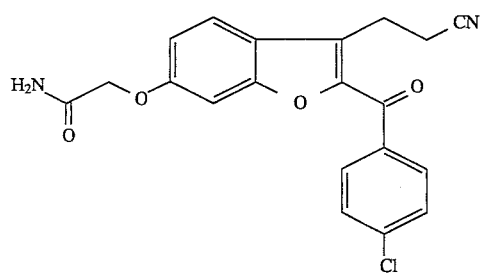

The title compound is prepared according to example 65.

EXAMPLE 290

3-[2-(4-Chloro-benzoyl)-6-hydroxy-benzofuran-3-yl]-propiohydroxamic acid

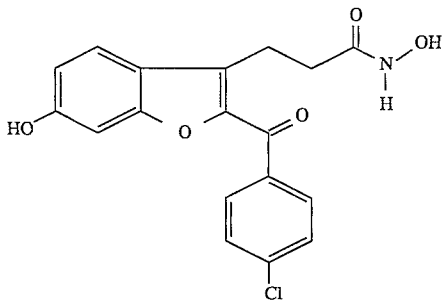

0.9 g (2.6 mmol) of the acid from example 58 were dissolved in THF. 1.85 g (11.1 mmol) carbonyl diimidazole were added and the reaction mixture was stirred at room temperature for 12 hours. 0.36 g (5.22 mmol) hydroxylamine hydrochloride were added and the mixture was stirred further 6 hours. The solvent was removed in vacuo and the residue was solved in ethylacetate. The organic phase was washed three times with water and one time with a NaHCO₃-solution and with a NaCl-solution. The organic phase was dried with Na₂SO₄ and concentrated in vacuo. The residue was further purified by chromatography.

Yield: 140 mg (15%) $R_f$: 0.29, V

We claim:

1. A benzofuranyl- and thiophenyl-alkane-carbonylic acid derivative of the formula

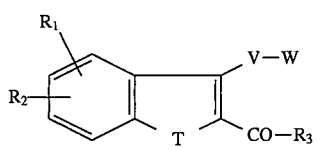

wherein

R¹ denotes hydrogen,

R² represents fluorine, chlorine, bromine, carboxyl, nitro, trifluoromethyl or a group of a formula —OR⁴, in which R⁴ denotes hydrogen, tetrahydropyranyl, benzyl, acetyl, cyclopropyl, cyclopentyl, cyclohexyl, which are optionally substituted by identical or different substituents selected from the group consisting of fluorine, chlorine, bromine, cyano, nitro or straight-chain or branched alkyl having up to 4 carbon atoms or denotes a residue of the formula

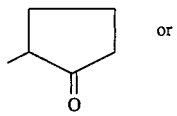

denotes straight-chain or branched alkyl or alkenyl each having up to 5 carbon atoms, and each of which is optionally monosubstituted disubstituted by identical or different substituents where the substituents are fluorine, chlorine, bromine, cyano, carboxy, straight-chain or branched alkoxy, alkoxycarbonyl or acyl each having up to 4 carbon atoms or by phenyl, where all cycles are optionally monosubstituted to disubstituted by identical or different substituents wherein the substituents are nitro, fluorine, chlorine, bromine, carboxy or straight-chain or branched alkoxycarbonyl having up to 4 carbon atoms, or alkyl or alkenyl are substituted by a group or formula —CO—NR⁸R⁹ in which R⁸ and R⁹ are identical or different and denote hydrogen, straight-chain or branched alkyl having up to 3 carbon atoms or phenyl, T represents an oxygen or sulfur atom V represents a straight-chain or branched alkylene or alkenylene chain each having 2 to 5 carbon atoms, W represents carboxy or a group of a formula —CO—R¹⁰, —CO—NR¹¹R¹², —CONR¹³—SO₂—R¹⁴ or PO(OR¹⁵)(OR⁶), in which R¹⁰ denotes hydroxyl, cycolpropyloxy, cyclopentyloxy, cyclohexyloxy or straight-chain or branched alkoxy having up to 5 carbon atoms, R¹¹, R¹² and R¹³ are identical or different und represent hydrogen, a straight-chain or branched alkyl having up to 3 carbon atoms or phenyl, or R¹¹ and R¹² together with the nitrogen atom form pyrrolidinyl or piperidinyl ring, R¹⁴ denotes a straight-chain or branched alkyl having up to 4 carbon atoms, which is optionally substituted by phenyl or trifluoromethyl, or R¹⁵ and R¹⁶ are identical or different and represent hydrogen or straight-chain or branched alkyl having up to 5 carbon atoms, R³ represents phenyl, which is monosubstituted to trisubstituted by identical or different subsituents wherein the substituents are hydroxyl, fluorine, chlorine, bromine, nitro, tetrazolyl, trifluoromethyl, difluoromethyl, cyano, carboxy, straight-chain or branched alkyl, alkoxy, alkoxycarbonyl or acyl each having up to 5 carbon atoms or by a group of formula —NR¹⁷R¹⁸ in which R¹⁷ and R¹⁸ have the meaning shown above for R¹¹ and R¹² and are identical to the latter or different from the latter, or R¹⁷ denotes hydrogen and R¹⁸ denotes straight-chain or branched acyl having up to 5 carbon atoms or a pharmaceutically acceptable salt thereof.

2. A compound according to claim 1, wherein T is oxygen.

3. A compound according to claim 1, wherein

R² is OR⁴, in which

R⁴ represents hydrogen, tetrahydropyranyl or C₁-C₅ straight-chain or branched alkyl, R³ represents phenyl, which is monosubstituted to trisubstituted by identical or different substituents selected from the group consisting of hydroxyl, fluorine, chlorine, bromine, nitro, tetrazolyl, trifluoromethyl, difluoromethyl, cyano, carboxy, straight-chain or branched alkyl, alkoxy, alkoxycarbonyl, or acyl, each having up to 5 carbon atoms, V represents alkylene, and W represents —CO—R¹⁰.

4. A compound according to claim 1 wherein such compound is 2-(4-Bromo-benzoyl)-6-[(tetrahydro-2H-pyran-2-yl)oxy]-3-benzofuranpropanoic acid methylester of the formula

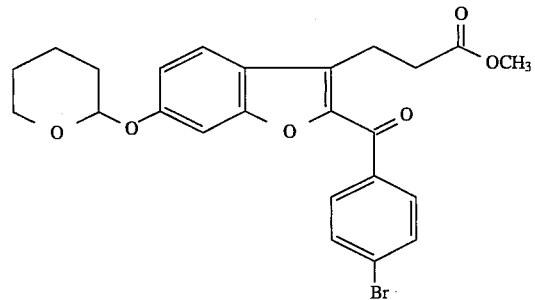

or a salt thereof.

5. A compound according to claim 1 wherein such compound is 2-(4-Bromo-benzoyl)- 6-hydroxy-3-benzofuranpropanoic acid methylester of the formula

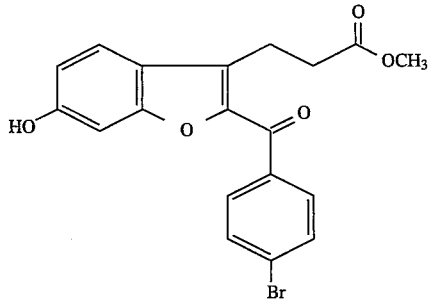

or a salt thereof.

6. A compound according to claim 1 wherein such compound is 6-Hydroxy-2-(-methyl-benzoyl)-3-benzofuranpropanoic acid of the formula

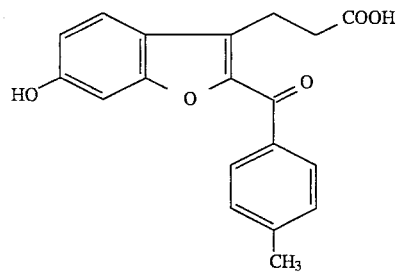

and salts thereof.

7. A compound according to claim 1 wherein such compound is 2-(4-Cyano-benzoyl)-6-methoxy-3-benzofuranpropanoic acid methylester of the formula

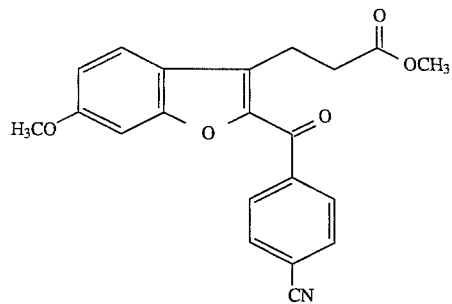

or a salt thereof.

8. A compound according to claim 1 wherein such compound 6-Methoxy-2-(4-tetrazolyl-benzoyl)-3-benzofuranpropanoic acid methylester of the formula

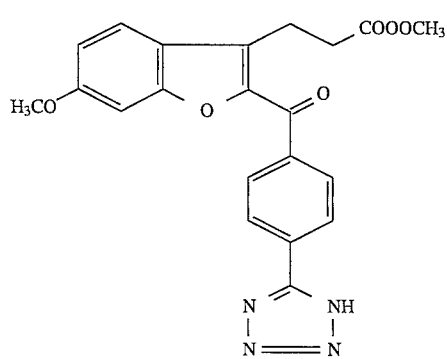

or a salt thereof.

9. A compound according to claim 1 wherein such compound is 6-Hydroxy-2-(4-methyl-benzoyl)-3-benzofuranpropanamide of the formula

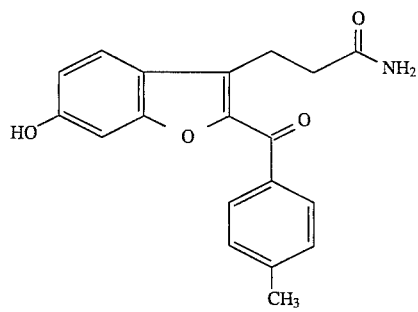

or a salt thereof.

10. A composition for the treatment and prevention of acute and chronic inflammatory processes comprising an amount effective therefore of a compound or salt thereof according to claim 1 and a pharmacologically acceptable diluent.

11. A method of treating and preventing inflammatory processes in a patient in need thereof which comprises administering in such patient an amount effective therefore of a compound or salt thereof according to claim 1.

* * * * *

UNITED STATES PATENT AND TRADEMARK OFFICE
CERTIFICATE OF CORRECTION

PATENT NO.  : 5,504,213
DATED       : April 2, 1996
INVENTOR(S) : Fischer, et al.

It is certified that error appears in the above-indentified patent and that said Letters Patent is hereby corrected as shown below:

Col. 59, line 30   After " monosubstituted " insert -- to --

Col. 61, line 19   Delete " and salts " and substitute -- or a salt --

Signed and Sealed this

Tenth Day of September, 1996

Attest:

BRUCE LEHMAN

Attesting Officer    Commissioner of Patents and Trademarks